United States Patent

Gandolfi et al.

Patent Number: 5,773,465
Date of Patent: Jun. 30, 1998

[54] TARTRONIC ACIDS, THEIR ACETALIC ETHERS AND O-ESTERS

[75] Inventors: Carmelo A. Gandolfi; Lorella Cotini; Marco Mantovanini; Gianfranco Caselli; Gaetano Clavenna; Claudio Omini, all of Milan, Italy

[73] Assignee: Dompé Farmaceutici S.p.A., Milan, Italy

[21] Appl. No.: 814,903

[22] Filed: Mar. 12, 1997

Related U.S. Application Data

[62] Division of Ser. No. 424,471, May 23, 1995, Pat. No. 5,656,656.

[30] Foreign Application Priority Data

Nov. 5, 1992 [IT] Italy ............................... MI92A02533
Jun. 21, 1993 [IT] Italy ............................... MI93A01330

[51] Int. Cl.$^6$ ....................... A61K 31/225; A61K 31/23; A61K 31/325; C07C 271/22
[52] U.S. Cl. ....................... 514/478; 514/485; 554/110; 554/112; 560/29; 560/160; 562/555
[58] Field of Search ................. 560/160, 29; 514/478, 514/485; 562/555; 554/110, 112

[56] References Cited

PUBLICATIONS

Mannich et al., Chem. Ber., 55 (1922) 3506–3508.
Chemical Abstracts, vol. 115, No. 21, 1991, Abstract No. 232008e, Jurczak, et al, "The High Pressure Reaction of 2,5–Dimethylfuran with Activated Carbonyl Compounds".
Tetrahedron Letters, vol. 25, No. 50, 1984, pp. 5747–5750, Genner, et al, "Reactions of Furans, Thiophenes and Pyrroles with Activated Carbonyl Compounds Under Thermal and High Pressure Conditions" (see pp. 5747–5748).
Chemical Abstracts, vol. 72, No. 9, 1970, Abstract No. 42684t, J. Grandjean, "Tartronic Acids", p. 352.
Bulletin of the Chemical Society of Japan, vol. 48, No. 1, 1975, pp. 277–280, Pac, et al, "Benzoyl Peroxide– And Photo–Induced Reactions of Diethyl Mesoxalate in Cyclohexane and Toluene" (see pp. 277–279).
Chemical Abstracts, vol. 51, No. 10, 1957, Abstract No. 12085g, Mikhlina, et al, "Synthesis of 3–Methyl–2–Quinclidinecarboxylic Acid".
Tetrahedron Letters, vol. 30, No. 10, 1989, pp. 1289–1292, Citterio, et al, "Oxidative Deprotonation of Carbonyl Compounds by FE(III)Salts" (see pp. 1289–1292).
Tetrahedron, (Incl. Tetrahedron Reports), vol. 25, No. 20, 1969, pp. 4967–4981, Chottard, et al, "Cyclisation Radicalaires.XII" (see pp. 4976–4981).
Liebigs Annalen Der Chemie, vol. 2, 1990, pp. 181–183, Kawabata, et al, "Electrochemical Hydroxylation of Active Methine Compounds" (see pp. 181–183).
Chemical Abstracts, vol. 85, No. 24, 1976, Abstract No. 179401m, Abe, et al, "Dibasic Acids Containing Ether Linkages" (p. 102).

*Primary Examiner*—José G. Dees
*Assistant Examiner*—Laura L. Stockton
*Attorney, Agent, or Firm*—Griffin, Butler Whisenhunt & Szipl

[57] ABSTRACT

Tartronic acid acetalic ethers and esters of the general formula:

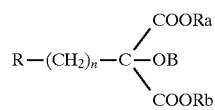

are provided and are useful in treatment of bone dysmetabolism. As examples, Ra and Rb may be hydrogen, B is a $C_2$–$C_{12}$ acyl group, R is phenyl and n is 0–12.

17 Claims, No Drawings

5,773,465

TARTRONIC ACIDS, THEIR ACETALIC ETHERS AND O-ESTERS

This application is a divisional application of Ser. No. 08/424,471, filed May 23, 1995, now U.S. Pat. No. 5,656,656.

SUMMARY OF THE INVENTION

The present invention relates to tartronic acid derivatives of general formula (I):

$$R-(CH_2)_n-C\begin{array}{c}COORa\\OB\\COORb\end{array}$$

in which:

Ra and Rb are independently hydrogen, an alkali or alkaline-earth metal, an ammonium or $C_1$–$C_{10}$ alkylammonium cation, a $C_1$–$C_4$ alkyl group, a $C_1$–$C_4$ alkoxyethyl, allyl or p-methoxybenzyl group;

B is hydrogen, a $C_2$–$C_{12}$ acyl group or an acetalic. moiety of formula (II):

$$\begin{array}{c}O\\\diagdown\\\diagup\\\phi\end{array}\qquad(II)$$

in which φ is selected from the group consisting of —$CH_2$—, O, S;

R is selected from phenyl; 4-biphenyl; 3,4,5-tri-$C_1$–$C_4$ alkoxyphenyl; 3,5-di-$C_1$–$C_4$-alkoxyphenyl; 4-hydroxy-3,5-di-$C_1$–$C_4$-alkoxyphenyl and the $C_1$–$C_7$ acyloxy derivatives thereof; 4-hydroxy-3,5-di-tert-butylphenyl; 3,5-di-tri-fluoromethylphenyl; fur-2-yl; 5-dimethylaminomethyl-fur-2-yl; α-, β- and γ-pyridyl; β- and β-naphthyl; γ-and β-naphthyloxymethyl; 2- and 3-quinolinyl; 2- and 3-(7-chloro-quinolinyl); m- and p-(2-quinolinylmethoxy)phenyl; m- and p-(7-chloro-2-quinolinylmethoxy)phenyl; 6-(2-quinolinylmethoxy)-β-naphthyl and 6-(7-chloro-2-quinolinylmethoxy)-β-naphthyl; phenylthio; $C_1$–$C4$-alkoxyphenylthio; 4-chlorophenylthio; 3,5-dimethyl-isoxazol-5-yl; 2-thienyl; 1,3-dioxolan-2-yl; 7-methoxy-cumarin-4-yl; 6,7-dimethoxy-cumarin-4-yl; a 4-oxo-thiazolidin-3-yl group substituted at the 2-position with a phenyl ring optionally having 1 to 3 substituents, which are the same or different, selected from hydroxy, $C_1$–$C_4$ alkoxy, $C_1$–$C_4$ alkyl, $C_1$–$C_4$ acyloxy; $C_1$–$C_{12}$ alkyl; $C_2$–$C_{12}$ alkenyl or alkynyl; $C_3$–$C_{12}$ cycloalkyl or cycloalkenyl; or a group of formula (III):

$$(R_2,R_3)N-(CH_2)_m-C(R_1)H-\qquad(III)$$

in which $R_1$ can be hydrogen, $C_1$–$C_4$ alkyl, phenyl or benzyl;

$R_2$ and $R_3$, independently from each other, are hydrogen, $C_1$–$C_4$ alkyl, tert-butoxycarbonyl (BOC), 9-fluorenylmethoxycarbonyl (FMOC), benzyloxycarbonyl, p-methoxybenzyloxycarbonyl, aminocarbonyl, $C_1$–$C_4$ alkylaminocarbonyl; or $R_2$ and $R_3$, taken together with the nitrogen atom they are linked to, form a 5 to 7 membered nitrogen heterocycle of formula (IV):

$$-N\begin{array}{c}(CH_2)_2\\\diagdown\\\diagup\\(CH_2)_p\end{array}X\qquad(IV)$$

wherein X is a bond between 2 carbon atoms, or is selected from the group consisting of —$CH_2$—, O, S, N—Rc, wherein Rc can be hydrogen, $C_1$–$C_4$ alkyl, $C_1$–$C_4$ alkoxycarbonyl, aminocarbonyl, BOC, FMOC, benzyloxycarbonyl, p-methoxybenzyloxycarbonyl, phenyl, benzyl, benzhydryl; or when $R_3$ is selected from hydrogen, $C_1$–$C_4$ alkyl, $C_1$–$C_4$ acyl, aminocarbonyl, $C_1$–$C_4$ alkoxycarbonyl, benzyl, p-methoxybenzyl, $R_1$ and $R_2$, taken together with the N and C atoms they are linked to, form a 5 to 7 membered nitrogen heterocycle;

m is zero or an integer from 1 to 3;

n is zero o an integer from 1 to 12;

p is the integer 2 or 3;

with the proviso that m and n cannot be at the same time zero when Ra, Rb, B and $R_1$ are H and $R_2$ and $R_3$ are independently hydrogen, methyl, or they form a piperidino group; the optically active forms, enantiomers, diastereomers thereof and related mixtures,. the pharmaceutically acceptable salts thereof, as medicinal agents against osteoporosis and bone dysmetabolism.

The compounds specifically excluded from general formula (I) are described by Mannich and Bauroth (Berichte, 55 (1922) 3504), who, on the other hand, indicate no therapeutic uses which, on the contrary, is within the scope of the present invention together with the compounds of formula (I).

These compounds of formula (I) are where:

Ra and Rb are methyl, B is hydrogen, n is 1, R is 5-methyl-fur-2-yl;

Ra and Rb are methyl, B is hydrogen, n is zero or 1, R is phenyl;

Ra and Rb are both hydrogen or ethyl, B is hydrogen, n is 1, R is phenyl;

Ra and Rb are ethyl, B is hydrogen, n is 3, R is phenyl;

Ra and Rb are ethyl, B is acetyl, n is 2, R is phenyl;

Ra is hydrogen, Rb is ethyl, B is acetyl, n is 3, R is phenyl;

Ra and Rb are hydrogen, B is hydrogen, n is 3, R is phenyl;

These compounds are known from Tetrahedron Lett. 25 (50), 1984, 5747; Chem. Abstr. 72 (9), 1970, N. 42684t; Bull. Chem. Soc. Jap. 48 (1), 277; Tetrahedron Lett. 30 (10), 1989, 1289; Tetrahedron Lett. 25 (20), 1969, 4976; Liebigs Ann. Chemie 2 (1990), 181.

The invention refers also to the compounds of formula (I) from which the above-mentioned compounds have been disclaimed.

The invention also relates to a process for the preparation of the compounds of formula (I) and pharmaceutical compositions containing them.

DESCRIPTION OF PREFERRED EMBODIMENTS

Examples of $C_1$–$C_4$ alkyl groups are: methyl, ethyl, propyl, iso-propyl, butyl, iso-butyl, tert-butyl, preferably methyl, ethyl, tert-butyl.

Examples of $C_1$–$C_4$-alkoxyethyl groups are: methoxyethyl, ethoxyethyl, propoxyethyl, iso-propoxyethyl, butoxyethyl, tert-butoxyetayl; preferably methoxyethyl.

Examples of $C_2$–$C_{11}$ acyl groups are: acetyl, propionyl, butyryl, iso-butyryl, valeryl, pivaloyl, caprinyl, lauroyl, benzoyl, phenylacetyl, phenylpropionyl; preferably benzoyl.

Examples of $C_1$–$C_{11}$ alkoxycarbonyl groups are: methoxycarbonyl, ethoxycarbonyl, propoxycarbonyl, tert-butoxycarbonyl, heptyloxycarbonyl, decyloxycarbonyl, preferably tert-butoxycarbonyl (Boc).

Examples of $C_1$–$C_4$ aminocarbonyl groups are: methylaminocarbonyl, ethylaminocarbonyl, butylaminocarbonyl, preferably methylaminocarbonyl.

Examples of heterocycles of formula (IV) are: pyrrolidine, piperidine, piperazine, 4-substituted piperazine, morpholine, thiomorpholine, azepine, oxazepine, thiazepine.

Preferred examples of cations are those of lithium, sodium, potassium, magnesium, ammonium, triethylatmmonium, tromethamine, or those of amino acids such as glycine, lysine, valine, leucine, isoleucine, cysteine and methionine.

In compounds of formula (I), $C_1$–$C_4$ alkoxyphenyl is preferably methoxyphenyl, $C_1$–$C_7$ acyloxyphenyl is preferably formyloxyphenyl or acetoxyphenyl, $R_1$ is preferably H, the $NR_2R_3$ group is preferably $NH_2$, methylamino, ethylamino, isopropylamino, dimethylamino and diethylamino; or $R_2$ and $R_3$ form a pyrrolidin-1-yl, piperidin-1-yl, morpholin-4-yl, thiamorpholin-4-yl, piperazin-1-yl group or a 4-ureido-, 4-methyl-, 4-phenyl-, 4-benzyl- or 4-benzhydryl- piperazin-1-yl residue.

When B is hydrogen or $C_2$–$C_{12}$ acyl, R is preferably a group of formula (III). $R_1$ is preferably hydrogen and one of $R_2$ or $R_3$ is hydrogen and the other is hydrogen, tert-butoxycarbonyl, $C_1$–$C4$-alkylaminocarbonyl, benzyloxycarbonyl.

When the carboxy groups of the compounds of formula (I) are in undissociated, or esterified, form, the $NR_2R_3$ basic group can be salified with a non toxic acid, for example organic acids such as acetic, trifluoroacetic, formic, propionic, fumaric, maleic, malic, malonic, benzoic, salicylic, 3,4,5-trimethoxybenzoic, methanesulfonic, benzenesulfonic, camphorsulfonic, lactic, aspartic, glutamic, 1- or d-thiazolidine-2-carboxylic, cysteine, N-acetyl-cysteine, carboxymethylcysteine; or inorganic acids such as phosphoric, sulfuric, hydrochloric and hydrobromic acids.

Particularly preferred acetalic ethers of the invention are 2-(1,4-dioxanylethers) and 2-tetrahydropyranyl ethers.

When B is the residue of an acetalic ether of formula (II), the preferred meaning for $C_1$–$C_{12}$ alkyl is methyl, the preferred meaning for $C_2$–$C_{12}$ alkenyl or alkynyl is vinyl or propargyl, the preferred meaning for $C_3$–$C_{12}$ cycloalkyl or cycloalkenyl is cyclopentyl, cyclohexyl, norborn-2-en-syn-7-yl.

Most preferred compounds of the invention are the acetalic ethers and the aglycons thereof of formula (I) in which n is an integer from 1 to 3 and R is as defined above.

The compounds of formula (I) in which B is a residue of an acetalic ether are per se useful agents in the therapy of bones dysmetabolism and moreover they are particularly useful intermediates for the synthesis of compounds of formula (I) in which B is hydrogen; moreover, said compounds are therapeutically effective as prodrugs of the above mentioned compounds in the therapy of bones dysmetabolism.

Similarly, the compounds I wherein B is a $C_2$–$C_{12}$ acyl group may be used either as active principles per se or as pro-drugs.

Specific examples of the compounds of the invention are the following acids:

3-(3,4,5-trimethoxyphenyl)-2-(2-tetrahydropyranyloxy)-2-carboxy-propanoic,
3-(4-hydroxy-3,5-dimethylphenyl)-2-(2-tetrahydropyranyloxy)-2-carboxy-propanoic,
3-(4-hydroxy-3 5-ditert-butylphenyl)-2-(2-tetrahydropyranyloxy)-2-carboxy-propanoic,
3-(3,5-ditrifluoromethylphenyl)-2-(2-tetrahydropyranyloxy)-2-carboxy-propanoic,
3-(3,5-ditrifluoromethylphenyl)-2-(2-1,4-dioxanyloxy)-2-carboxy-propanoic,
3-(3,5-ditrifluoromethylphenyl)-2-(2-1,4-oxathianyloxy)-2-carboxy-propanoic,
3-(5-dimethylamino-fur-2-yl)-2-(2-tetrahydropyranyloxy)-2-carboxy-propanoic,
3-(2-pyridyl)-2-(2-tetrahydropyranyloxy)-2-carboxypropanoic,
3-(3-pyridyl)-2-(2-tetrahydropyranyloxy)-2-carboxypropanoic,
3-(4-pyridyl)-2-(2-tetrahydropyranyloxy)-2-carboxypropanoic,
3-(3-pyridyl)-2-(1,4-dioxan-2-yloxy)-2-carboxypropanoic,
4-α-naphthyloxy-2-(2-tetrahydropyranyloxy)-2-carboxybutanoic,
4-β-naphthyloxy-2-(2-tetrahydropyranyloxy)-2-carboxybutanoic,
3-(2-quinolinyl )-2-(2-tetrahydropyranylaxy)-2-carboxypropanoic,
3-(3-quinolinyl)-2-(1,4-dioxan-2-yloxy)-2-carboxypropanoic,
3-(7-chloro-quinolin-2-yl)-2-(2-tetrahydropyranyloxy)-2-carboxy-propanoic,
3-(7-chloro-quinolin-3-yl )-2-(1,4-dioxan2-yloxy)-2-carboxy-propanoic,
3-(4-(2-quinolinemethoxy)phenyl)-2-(2-tetrahydropyranyloxy)-2-carboxy-propanoic,
3-(3-(2-quinolinemethoxy)phenyl)-2-(1,4-dioxan-2-yloxy)-2-carboxy-propanoic,
3-(4-(7-chloro-2-quinolinemnethoxy) phenyl)-2-(2-tetrahydropyranyloxy)-2-carboxy-propanoic,
3-(3-(7-chloro-2-quinolinemethoxy) phenyl)-2-(2-tetrahydropyranyloxy)-2-carboxypropanoic
3-(6-(2-quinolinemethoxy)-β-naphthyl )-2-(2-tetrahydropyranyloxy)-2-carboxy-propanoic,
3-(6-(7-chloro-2-quinolinylmethoxy)-β-naphthyl)2-(2-tetrahydropyranyloxy)-2-carboxy-propanoic
3-(phenylthio)-2-(2-tetrahydropyranyloxy)-2-carboxy-propanoic,
3-(4-methoxyphenylthio)-2-(2-tetrahydropyranyloxy)-2-carboxy-propanoic,
3-(4-chlorophenylthio)-2-(2-tetrahydropyranyloxy)-2-carboxy-propanoic,
3-(3,5-dimnethyl-isoxazol-5-yl)-2-(2-1,4-dioxanyloxy)-2-carboxy-propanoic,
3-(3,5-dimethyl-isoxazol-5-yl)-2-(2-tetrahydropyranyloxy)-2-carboxy-propanoic,
3-(7-methoxy-cumarin-4-yl)-2-(2-tetrahydropyranyloxy)-2-carboxy-propanoic,
3-(6,7-dimethoxy-cumarin-4-yl)-2-(2-tetrahydropyranyloxy)-2-carboxy-propanoic,
3-(3,4,5-trimethoxyphenyl)-2-hydroxy-2-carboxy-propanoic,
3-(4-hydroxy-3,5-dimethylphenyl)-2-hydroxy-2-carboxy-propanoic,
3-(4-hydroxy-3,5-ditert-butylphenyl)-2-hydroxy-2-carboxy-propanoic,
3-(3,5-ditrifluoromethylphenyl)-2-hydroxy-2-carboxy-propanoic, 3-(5-dimethylamino-fur-2-yl)-2-hydroxy-2-carboxy-propanoic,
4-α-naphthyloxy-2-hydroxy-2-carboxy-butanoic,
4-β-naphthyloxy-2-hydroxy-2-carboxy-butanoic,
3-(2-quinolinyl)-2-hydroxy-2-carboxy-propanoic,
3-(3-quinolinyl)-2-hydroxy-2-carboxy-propanoic,
3-(7-chloro-quinolin-2-yl)-2-hydroxy-2-carboxy-propanoic,
3-(7-chloro-quinolin-3-yl)-2-hydroxy-2-carboxy-propanoic,
3-(4-(2-quinolinemethoxy)phenyl)-2-hydroxy-2-carboxy-propanoic,
3-(3-(2-quinolinemethoxy)phenyl)-2-hydroxy-2-carboxy-propanoic,
3-(4-(7-chloro-2-quinolinemethoxy)phenyl)-2-hydroxy-2-carboxy-propanoic,
3-(3-(7-chloro-2-quinolinemethoxy)phenyl)-2-hydroxy-2-carboxy-propanoic,
3-(7-(2-quinollinemethoxy)-β-naphthyl)-2-hydroxy)-2-carboxy-propanoic,
3-(7-(7-chloro-2-quinolinylmethoxy)-β-naphthyl)-2-hydroxy-2-carboxy-propanoic,
3-(phenylthio)-2-hydroxy-2-carboxy-propanoic,
3-(4-methoxyphenylthio)-2-hydroxy-2-carboxy-propanoic,
3-(4-chlorophenylthio)-2-hydroxy-2-carboxy-propanoic,
3-(3,5-dimethyl-isoxazol-5-yl)-2-hydroxy-2-carboxy-propanoic,
3-(7-methoxy-cumarin-4-yl)-2-hydroxy-2-carboxy-propanoic,
3-(6,7-dimethoxy-cumarin-4-yl)-2-hydroxy-2-carboxy-propanoic,
4-amino-2-(2-tetrahydropyranyloxy)2-carboxybutanoic,
5-tert-butoxycarbonyl-2-(2-tetrahydropyranyloxy)-2-carboxy-pentanoic,
5-FMOC-amino-2-(tetrahydropyranyloxy)-2-carboxy-pentanoic,
8-benzyloxycarbonylamino-2-(2-tetrahydropyranyloxy)-2-carboxy-octanoic,
8-amino-2-(2-tetrahydropyranyloxy)-2-carboxy-octanoic,
4-(pyrrolidin-1-yl)-2-(2-tetrahydropyranyloxy)-2-carboxy-butanoic,
4-(piperidin-1-yl)-2-(2-tetrahydropyranyloxy)-2-carboxy-butanoic,
4-(morpholin-4-yl)-2-(2-tetrahydropyranyloxy)-2-carboxy-butanoic,
4-(pyrrolidin-1-yl)-2-(1,4-dioxan-2-yloxy)-2-carboxy-butanoic,
4-(piperidin-1-yl)-2-(1,4-dioxan-2-yloxy)-2-carboxy-butanoic,
4-(morpholin-4-yl)-2-(1,4-dioxan-2-yloxy)-2-carboxy-butanoic,
(R,S) 3-(1-p-methoxycarbobenzyloxy-pyrrolidin-2-yl)-2-(tetrahydro-pyranyloxy)-2-carboxy-propanoic and the (R) and (S) enantiomers thereof,
(R,S) 4-(1-p-methoxycarbobenzyloxy-pyrrolidin-2-yl)-2-(tetrahydro-pyranyloxy)-2-carboxy-butanoic and the (R) and (S) enantiomers thereof,
2-hydroxy-2-carboxy-4-amino-butanoic,
2-hydroxy-2-carboxy-5-tert-butoxycarbonylamino-pentanoic,
2-hydroxy-2-carboxy-5-amino-pentanoic,
2-hydroxy-2-carboxy-8-amino-octanoic,
2-hydroxy-2-carboxy-4-(pyrrolidin-1-yl)-butanoic,
2-hydroxy-2-carboxy-4-(piperidin-1-yl)-butanoic,
2-hydroxy-2-carboxy-4-(morpholin-4-yl)-butanoic,
(R), (S), and (R,S) 2-hydroxy-2-carboxy-4-(pyrrolidin-2-yl)-butanoic,
(R), (S), and (R,S) 2-hydroxy-2-carboxy-4-(piperidin-2-yl)-butanoic,
(R), (S), and (R,S) 2-hydroxy-2-carboxy-4-(piperidin-3-yl)-butanoic,
2-hydroxy-2-carboxy-4-(piperidin-4-yl)-butanoic,
2-hydroxy-2-carboxy-4-(pyrid-3-yl)-butanoic;
ethyl 5-Boc-amino-2-benzoyloxy-2-ethoxycarbonyl-pentanoate;
ethyl 2-benoyloxy-2-ethoxycarbonyl-3 (pyrid-2-yl) propionate;
and the methyl, ethyl, allyl, 2-methoxyethyl and p-methoxybenzyl esters as well as the hemi-esters thereof.

The compounds of general formula (I) are obtained by alkylation of tartronic or malonic acid esters of formula (V):

in which Ra' and Rb' can be $C_1$–$C_4$ alkyl, $C_1$–$C_4$-alkoxy-ethyl, allyl or p-methoxybenzyl and X is hydrogen or an acetalic residue selected from tetrahydropyran-2-yloxy, 1,4-dioxan-2-yloxy and 1,4-oxathian-2-yloxy with a compound of formula (VI):

in which R is as defined above and W is selected from the group consisting of chlorine, bromine, iodine, or a sulfonic ester such as mesylate, p-toluenesulfonate, benzenesulfonate, trifluoromethanesulfonate, to give a diester of formula (Ia):

wherein R, Ra', Rb', and X are as defined above; subsequently, if X is an acetalic residue (tartronic esters) the compound of formula (Ia) can be transformed into a compound of formula (I), for example by means of transesterification reactions, elimination of the protecting groups, N-alkylation or acylation. The tartronic diesters of formula (Ia) can be hydrolysed or transformed into tartronic acid derivatives which are then recovered as salts or free acids or re-esterified with a suitable RaOH or RbOH alcohol or mixtures thereof.

On the contrary, when X is hydrogen (malonic esters), the compounds of formula (Ia) can be transformed into compounds (I) by reaction with a $C_2$–$C_{12}$ acyl peroxide, followed by selective transesterification in the presence of an alkali or earth-alkaline carbonate and of the desired alcohol, in anhydrous conditions.

The compounds of formula (V) in which X is an acetalic residue can be obtained starting from tartronic diesters of formula (VII)

using well known methods such as the reaction in an aprotic solvent with a vinyl ether selected from the group of dihydropyran, 1,4-dioxene and 1,4-oxathiene in the presence of Lewis acids such as $POCl_3$, $BF_{31}$ etherated $BF_3$, a sulfonic acid such as p-toluenesulfonic, benzenesulfonic, methanesulfonic, trifluoromethanesulfonic acids and the pyridinium salts thereof. Examples of suitable aprotic solvents are dichloromethane, chloroform, benzene, toluene, ethyl and methyl acetate and the mixtures thereof; alternatively, the vinyl ether itself can be used as the solvent.

The tartronic diesters of formula (VII) are commercially available or can be prepared from commercially available products. The compounds of formula (VI) are also commercially available or they can be prepared according to well-known methods.

The compounds of formula (Ia) are obtained by deprotonation of a compound of formula (V) by means of a suitable base and subsequent reaction with preferably equimolecular amounts or a molar excess of a compound of formula (VI) in a suitable solvent, operating in a temperature range from −80° C. to the solvent's reflux temperature. Preferably the reaction is carried out at a temperature from −10° C. to the solvent' reflux temperature, more preferably at room temperature. Suitable bases are alkali metals, alkali metal hydrides, alcoholates such as sodium methoxide, sodium ethoxide and potassium tert-butylate or amides such as sodium or potassium amides, alkyl and phenyl lithium, dialkylamino lithium derivatives, sodium bis-trimethylsilylamide. Preferred solvents are straight and branched $C_1$–$C_5$ alcohols, ethers such as dioxane and tetrahydrofuran, aromatic and non aromatic hydrocarbons such as benzene, toluene, hexane, pentane, heptane, aprotic solvents such as N-alkyl-pyrrolidones, dimethylformamide, dimethylsulfoxide and mixtures thereof: the choice of the solvent depends on the nature of the base selected for the deprotonation of the compound of formula (V) and on the reactivity of the alkylating agent of formula (VI).

The removal of primary- and secondary- amino protecting groups optionally present in compounds of formula (I) and (Ia) is performed using well known techniques: for example, the benzyl groups can be removed by hydrogenation in the presence of Pd catalysts, the FMOC groups in the presence of piperidine, whereas the tert-butoxycarbonyl groups are preferably removed with trifluoroacetic acid.

In any case, the removal of any protecting groups present in compounds of formula (Ia) with mineral acids and with organic acids, even weak ones, in protic solvents is combined with the hydrolysis or the transesterification of the hemiacetalic ether to give compounds of formula (I) in which X is hydroxy. Preferred desetherification conditions of a compound of formula (Ia) to give a compound of formula (I) in which X is hydroxy comprise the treatment of $C_1$–$C_5$ alcohol solutions of a compound of formula (Ia) with a Lewis acid, as described above (preferably p-toluenesulfonic acid), in amounts from catalytic to a molar excess, at a temperature from room temperature to the solvent's reflux temperature.

When desired, an acetalic ether of formula (I) can be converted into another acetalic ether of formula (I) by acetalyzing a 2-hydroxy derivative of formula (I) with the suitable cyclic vinyl ether selected from 2-dihydropyran, 1,4-diox-2-ene and 1,4-oxathi-2-ene.

The hydrolysis of the tartronic esters of the compounds of formula (Ia) is preferably performed with LiOH aqueous solutions in a $C_1$–$C_3$ alcohol, at temperatures from −10° C. to room temperature, in a time from some hours to 48 hours. Methanol is preferably used, in the presence of two molar equivalents or a slight excess of LiOH. Allyl esters can be removed in the presence of Pd-phosphine and an alkanoic acid alkali metal salt.

The transformation of a compound of formula (Ia) into one of formula (I) in which each of Ra, Rb, and X is hydroxy, can also be performed carrying out the hydrolysis of the ester groups before removing all the protecting groups optionally present.

A compound of formula (Ia) in which X is hydrogen can be transformed into a compound of formula (I) in which B is hydrogen or a $C_2$–$C_{12}$ acyl group by reaction with a suitable base and subsequent reaction with about equimolecular amounts of a $C_2$–$C_{12}$ acylperoxide, in an inert solvent, preferably at a temperature from −5° to +5° C. Preferred solvents are aromatic hydrocarbons such as benzene, toluene, chlorobenzene, xylene. Suitable bases are alkali metal hydrides, alcoholates such as sodium methoxide and potassium tert-butylate or amides such as sodium amide, potassium amide. Preferably, deprotonation can be carried out in situ by reacting a malonate of formula (Id) (X=H) with an alkali metal hydride, for example sodium hydride. The reaction is generally over in a time from several minutes to two hours. When a slight acylperoxide excess is used, the final addition of phosphines such as triphenylphosphine or tributylphosphine allows to destroy the reagent excess. Tertiary alcohols of formula (I), wherein B is H, are also obtained as side-products from the acylation reaction.

The obtained $C_2$–$C_{12}$ acyloxy derivatives may be subjected to transesterification by reaction with a suitable dry alcohol in the presence of an excess of an alkaline or earth-alkali carbonate, at a temperature from −10° C. to the room temperature, preferably from 0° to 10° C. The alcohol used in the transesterification is preferably the same which esterifies the carboxy groups of compounds Ia. The transesterification is preferably carried out in methanol so that compounds Ia are isolated as methylesters.

The compounds of the invention of formula (I) can be used in the treatment of osteoporosis and bones dysmetabolism, in the treatment of malignant hypercalcaemia and of Paget's syndrome.

Metabolic abnormities of the bone tissue are often characterized by a loss in the bone mass and they can due to both incapability of mineralising the matrix and inadequate matrix formation, which conditions are known under the names of osteomalacia and osteoporosis, respectively. The bone tissue is an active tissue, continuosly renewed, which balance depends on a suitable control of the growth and degradation thereof by osteoblasts and osteoclasts, which are cells exerting osteogenesis and osteolysis functions, respectively.

As far as osteoclasts role is concerned, they are well known to be the main responsible for bone resorption. Thus, for instance, when primary cultures of rabbit osteoclasts, enzymatically recovered, are grown on devitalised bovine bone slices, the formation of bone resorbing pits is observed.

It would be highly desirable to provide medicaments, which, in pathological and hyper-reactivity conditions, whilst keeping osteoclasts viable, could inhibit the osteolytic hyperfunctionality thereof, which is the capability of inducing bone resorbtion, i.e. of forming bone resorbing pits.

The compounds of the invention when tested in vitro, according to the protocol described by Y. Su et al., Endocrinology, 131, 1497, 1992, in a range of scalar concentrations from $10^{-13}$ to $10^{-4}$M, turned out to be particularly effective in inhibiting the formation of bone resorbing pits, without cytotoxic effects on the osteoclasts themselves. Compared with untreated controls, ethydronate, which is a bis-phosphonate used as the control drug, causes a bone resorption, evaluated according to the number (count) and to the consistency of the formed bone cavities, of only 58% of the control values for about $10^{-8}$M concentrations, whereas 74% inhibitions are observed only at high concentrations ($1\times10^{-4}$M).

On the contrary, its close dicarboxylic analogue: 2-hydroxy-2-methyl-1,3-propanedioic, already at $1\times10^{-10}$M concentrations reaches the maximum inhibition (73%), showing a 40% inhibition at about $10^{12}$M concentrations, so that an $EC_{50}$ of $1\times10^{-11}$M is calculated for the compound. Similar values for the $IC_{50}$s can be evaluated for 2-(1,4-dioxan-2-yloxy)-2-methyl-1,3-propanedioic acid and for the corresponding 2-(1,4-oxathian-2-yl) and 2-(2-tetrahydropyran-2-yl) acetalic ethers of 2-hydroxy-2-methyl-1,3-propanedioic acid.

Thus, for example, 5-tert-butoxycarbonylamino-2-hydroxy-2-carboxy pentanoic acid inhibits by 85% the activity of osteoclasts at a $1\times10^{-13}$M concentration and similar inhibitions can be evidenced for the corresponding hemiacetalic ethers. On the contrary, an inhibition of the osteoclastic activity of about 63% is measured for $1\times10^{-12}$M concentrations of methyl 5-amino-2-hydroxy-2-methoxycarbonyl-pentanoate.

The administration of the compounds of the invention occurs without adverse side-effects on bones growth and the mineralisation.

Particularly preferred compounds of the invention are the compounds of formula (I), in which Ra and Rb are different from hydrogen, showing an excellent bioavailability, after oral administration, which can at least be compared with that of the corresponding free acids, after parenteral administration.

Compared with the already known alkyl and aminoalkyl-gem-bisphosphonates, which are widely used in therapy, the compounds of the invention have the advantage of a better bioavailability by the oral route.

For the envisaged therapeutic uses, the compounds of the invention are suitably formulated in pharmaceutical compositions using conventional techniques and excipients, as described in "Remington's Pharmaceutical Sciences Handbook", Mack Publishing Co., New York, USA, 17th Ed., 1985. The compositions of the invention can be administered intramuscularly, intravenously, by bolus and orally, in form of capsules, tablets, syrups and optionally as controlled-release forms. The daily dosage will depend on various factors, such as severity of the disease and conditions of the patient (sex, weight, age): the dose will generally range from 10 to 1500 mg of the compounds per day, optionally divided in multiple administrations. Higher dosages, even for more prolonged times, can be administered thanks to the low toxicity of the compounds of the invention.

The following examples further illustrate the invention.

EXAMPLE 1

Diethyl 2-(tetrahydropyranyloxy)-1,3-propanedioate

4 Mg of p-toluenesulfonic acid monohydrate (pTS) are added to a solution of 4 g of ethyl tartronate (diethyl 2-hydroxy-1,3-propanedioate) and 2.67 g of 3,4-dihydropyran in dichloromethane (30 ml). The mixture is shielded from humidity and kept under slight stirring for 1 hour, then 2 drops of pyridine are added. The organic phase is washed repeatedly with a 5% sodium bicarbonate aqueous solution and water and is dried over sodium sulfate. By evaporation of the solvent, an oily mass of ethyl 2-(2-tetrahydropyranyloxy)-1,3-dioate (about 5 g) is obtained, which can be used either directly or after percolation on a $SiO_2$ column or after distillation. (TLC $SiO_2$, 30:70 AcOEt-cyclohexane, one spot at $R_f$ 0.41; developer: $I_2$ vapors). I.R. 2950, 1760 $cm^{-1}$.

Dimethyl 2-(1,4-dioxan-2-yloxy)-1,3-propanedioate 20 mg of pTS acid are added to a solution of 15 g of dimethyl tartronate (dimethyl 2-hydroxy-1,3-propanedioate) and 9.5 g of 1,4-diox-2-ene in dichloromethane (80 ml). The mixture is kept under slight stirring for 2 hours, shielded from humidity. 0.2 ml of pyridine are added, the organic phase is washed with water, 5% aqueous $NaHCO$ After drying, by evaporating to dryness the solvent under vacuum, an oily mass of methyl 2-(1,4-dioxan-2-yloxy)-propane-1,3-dioate (about 25 g) is obtained, which can be used either directly or after percolation on a $SiO_2$ column ($SiO_2$, 10:90 AcOEt-Cyclohexane) or after distillation. I.R.: 2950, 1760 $cm^{-1}$.

Di-2-methoxyethyl 2-(1,4-oxathian-2-yloxy)-1,3-propanedioate

One drop of methanesulfonic acid is added to a solution of 1.2 g of 1,4-oxathi-2-ene and 2.4 g of 2-methoxyethyl 2-hydroxy-1,3-propanedioate in 15 ml of dichloromethane, shielding from humidity for 3 hours. 0.2 ml of triethylamine are added; the organic phase is washed with water, 5% aqueous $NaHCO_3$ and, after drying, the solvent is evaporated to dryness under vacuum. After purification on silica gel (eluent $Et_2O$-cyclohexane), 2.67 g of 2-methoxyethyl 2-(1,4-oxatian-2-yloxy)-1,3-propanedioate are obtained.

Di-p-methoxybenzyl 2-(2-tetrahydropyranyloxy)-1,3-propanedioate 3 drops of $POCl_3$ are added to a solution of di-p-methoxybenzyl-2-hydroxy-tartronate (33.2 g) and 2-dihydropyran (9.3 g) in anhydrous benzene (60 ml). After 8 hours at room temperature, 0.2 ml of pyridine are added. The organic phase is washed repeatedly with a 5% $NaHCO_3$ aqueous solution and water. By evaporation of the solvent, an oily residue of di-p-methoxybenzyl 2-(2-tetrahydropyranyloxy)-1,3-propanedioate (40 g) is obtained which can be used without further purifications.

Diallyl 2-(2-tetrahydropyranyloxy)-1,3-propanedioate 15 mg of pTS acid are added to a solution of allyl 2-hydroxy-1,3-propanedioate (8 g) and 2-dihydropyran (3.6 g) in 20 ml of dichloromethane, to obtain 11 g of allyl 2-(2-tetrahydropyranyloxy)-1,3-propanedioate.

According to the above described procedures, the following compounds are obtained:

Dimethyl 2-(tetrahydropyranyloxy)-1,3-propanedioate
Di-2-methoxyethyl 2-(tetrahydropyranyloxy)-1,3-propanedioate
Diallyl 2-(1,4-dioxan-2-yloxy)-1,3-propanedioate
Diallyl 2-(1,4-oxathian-2-yloxy)-1,3-propanedioate
Dimethyl 2-(1,4-oxathian-2-yloxy)-1,3-propanedioate
Diethyl 2-(1,4-dioxan-2-yloxy)-1,3-propanedioate
Di-2-methoxyethyl 2-(1,4-dioxan-2-yloxy)-1,3-propanedioate
Diethyl 2-(1,4-oxathian-2-yloxy)-1,3-propanedioate
Di-p-methoxybenzyl 2-(1,4-dioxan-2-yloxy)-1,3-propanedioate
Di-p-methoxybenzyl 2-(1,4-oxathian-2-yloxy)-1,3-propanedioate

EXAMPLE 2

8 G of ethyl 2-(tetrahydropyranyloxy)-1,3-propanedioate dissolved in 5 ml of EtOH are added, under stirring, shielding from humidity, to a solution of sodium ethoxide, prepared dissolving 0.76 g of metal Na in 12 ml of absolute ethanol (EtOH), keeping the temperature at 0° to 5° C. A white precipitate forms, then a solution of 4 ml (5.6 g) of benzyl bromide in 10 ml of EtOH is added. At the end of the addition, stirring is continued for 90 min. more, to complete the C-alkylation reaction. Then the mixture is evaporated to dryness; the residue is partitioned between ethyl acetate (AcOEt) and a 20% $KH_2PO_4$ aqueous solution; the combined organic phases are dried over sodium sulfate. By evaporating to dryness the solvent under vacuum, 10.1 g of an oily residue of ethyl 3-phenyl-2-ethoxycarbonyl-2-(2-tetrahydropyranyloxy)-propanoate are obtained. A pure sample, obtained by chromatography ($SiO_2$, eluent: 10:90 AcOEt-hexane) shows I.R.: 2960, 1740, 1600, 1250 $cm^{-1}$; HNMR($CDCl_3$)δ (TMS): 1.2 t, 1.3 t, 1.6 m, 1.65–1.8 m, 1.9 m, 3.15 d, 3.35–3.55 d+m, 3,85–4.0 m, 4.0–4.3 2 m, 5.15–5.2 t, 7.3 s.

36.5 Ml of a LiOH alcohol aqueous solution (prepared dissolving 3 g of $LiOH.H_2O$ in 15 ml of water and diluting to 100 ml with methanol) are added, under stirring, to a solution of 3 g of ethyl 3-phenyl-2-ethoxycarbonyl-2-(2-tetrahydropyranyloxy)-propanoate in 20 ml of methanol. The mixture is kept under stirring, at room temperature (r.t.) for 2 hours; at the same time crystalline 3-phenyl-2-carboxy-2-(2-tetrahydropyranyloxy)-propanoic acid lithium salt precipitates, 1.8 g, m.p.>230° C.

25 mg of pTS acid are added to a solution of ethyl 3-phenyl-2-ethoxycarbonyl-2-(2-tetrahydropyranyloxy)-propanoate (6 g) in EtOH (25 ml). After 12 hours at r.t., the solvent is evaporated under vacuum, the mixture is partitioned between water and AcOEt; the organic phase is separated, dried, concentrated to small volume. The residue is adsorbed on $Sio_2$ (40 g); by elution with 90:10 cyclohexane:AcOEt, 4.3 g of ethyl 3-phenyl-2-hydroxy-2-ethoxycarbonyl-prooanoate, oil, are obtained. I.R.: 3500, 3000, 1740, 1600 $cm^{-1}$; HNMR ($CDCl_3$) δ (TMS): 1.2–1.35 t, 3.35 s, 3,15 s, 4.2–4.3 q, 7.25 s.

2 g of the ester are treated in MeOH with aqueous-methanol LiOH, as described above, to give 1.2 g of 3-phenyl-2-hydroxy-2-carboxy propanoic acid lithium salt, m.p.>300° C.:, I.R. 3400, 1640 $cm^{-1}$; HNMR (D20) δ (TMS): 3,4 s, 7.2–7.35 m.

EXAMPLE 3

A solution of 2.8 g of diallyl 2-(1,4-dioxan-2-yloxy)-1,3-propanedioate is added under stirring and nitrogen atmosphere to a suspension of 0.31 g of 80% NaH in mineral oil in 3 ml of N-methylpyrrolidone and 17 ml of benzene. The mixture is warmed to 30°–40° C. until the hydrogen evolution is over, then it is cooled to r.t.; then, dropwise, with a solution of 3,5-ditrifluoromethyl-benzyl bromide (3 g) in 15 ml of benzene is added to the sospension. The mixture is stirred for 8 h, then diluted with 15 ml of a 20% $NaH_2PO_4$ aqueous solution. The organic phase is separated, washed with water and dried over sodium sulfate. After evaporation of the solvent, the residue is purified by chromatography on $SiO_2$, eluent 90:10 cyclohexane:AcOEt, to give 3.45 g of allyl 3-(3,5-ditrifluoromethyl)phenyl-2-allyloxycarbonyl-2-(1,4-dioxan-2-yloxy)-propanoate.

EXAMPLE 4

According to the procedure of example 3, using 2.6 g of methyl 2-(1,4-oxathian-2-yloxy)-1,3-propanedioate, 2.81 g of methyl 3-(3,5-ditrifluoromethyl)phenyl-2-methoxycarbonyl-2-(1,4-oxathian-2-yloxy)-propanoate are obtained.

EXAMPLE 5

Analogously to examples 2 and 3, by reacting an appropriate benzylhalide or sulfonate with a deprotonated form of the following acetalic ethers: 2-(2-tetrahydropyranylether), 2-(1,4-dioxan-2-ylether) and 2-(l,4-oxathian-2-ylether) of as 2-hydroxy-1,3-propanedioic acid methyl, ethyl, allyl or p-methoxybenzyl ester, the acetalic ethers of the corresponding esters of the following acids are prepared:
3-phenyl-2-hydroxy-2-carboxy-propanoic,
3-(4-biphenyl)-2-hydroxy-2-carboxy-propanoic,
3-(3,4,5,-trimethoxy)phenyl-2-hydroxy-2-carboxy-propanoic,
3-(2-furyl)-2-hydroxy-2-carboxy-propanoic,
3-(2-thienyl)-2-hydroxy-2-carboxy-propanoic,
3-(α-naphthyl)-2-hydroxy-2-carboxy-propanoic,
3-(β-naphthyl)-2-hydroxy-2-carboxy-propanoic,
3-(3,5-dimethyl-isoxazol-5-yl)-2-hydroxy-2-carboxy-propanoic,
3-(4-formyloxy-3,5-dimethoxy)phenyl-2-hydroxy-2-carboxy-propanoic,
3-(4-acetoxy-3,5-di-tert-butyl)phenyl-2-hydroxy-2-carboxy-propanoic.

EXAMPLE 6

Analogously to examples 2 and 3, by reacting halides (preferably iodides, bromides) or sulfonates of $C_1$–$C_{12}$ alkyls or alkenyls or alkynyls, of $C_3$–$C_{12}$ cycloalkyls or cycloalkenyls with methyl, ethyl, allyl, or p-methoxybenzyl 2-(2-tetrahydropyranyloxy), 2-(1,4-dioxan-2-yloxy) or 2-(1, 4-oxathian-2-yloxy)-1,3-propa-nedioates, the corresponding acetalic ethers of the esters of the following acids are obtained:
2-hydroxy-2-methyl-1,3-propanedioic,
2-hydroxy-2-allyl-1,3-propanedioic,
2-hydroxy-2-(but-2-yn)-1,3-propanedioic,
2-hydroxy-2-cyclopentyl-1,3-propanedioic,
2-hydroxy-2-cyclopentylmethyl-1,3-propanedioic,
2-hydroxy-2-cyclohexylmethyl-1,3-propanedioic,
2-hydroxy-2-cyclopentylethyl-1,3-propanedioic,
2-hydroxy-2-cyclohexylethyl-1,3-propanedioic,
2-hydroxy-2-(nor-bon-2-en-*sin*-7-yl-methyl)-1,3-propanedioic,
which, if desired, are hydrolysed with LiOE in MeOH—$H_2O$ to give. the lithium salts thereof and the corresponding free acids.

EXAMPLE 7

A solution of 0.5 g of ethyl 3-(4-formyloxy-3,5-dimethoxy)phenyl-2-(2-tetrahydropyranyloxy)-2-ethoxycarbonyl-propanoate in EtOH (10 ml), added with 25 mg of pTS acid, is kept at r.t. for 12 hours. After evaporation to dryness, the residue is purified by chromatography on silica gel (eluent 30:70 cyclohexane-ethyl acetate) to give 0.22 g of ethyl 3-(4-hydroxy-3,5-dimethoxy)phenyl-2-hydroxy-2-ethoxvcarbonyl-propanoate.

EXAMPLE 8

A solution of 0.5 g of methyl 3-(4-acetoxy-3,5-di-tert-butyl)phenyl-2-(2-tetrahydropyranyloxy)-2-methylcarbonyl-propanoate in 5 ml of anhydrous MeOH, added with 80 mg of anhydrous potassium carbonate, is kept under stirring for 3 hours a room temperature. The insolubles are filtered off, the solvent excess is evaporated under vacuum; the residue is partitioned between ethyl acetate and water. The organic phase is washed with water to neutrality, then dried over sodium sulfate. By evaporation of the solvent, 0.18 g of methyl 3-(4-hydroxy-3,5-di-tert-butyl)phenyl-2-(2-tetrahydropyranyloxy)- 2-methylcarbonyl-propanoate are obtained. The alkali aqueous phases are combined and neutralized to pH 6.8, under strong stirring, in the presence of half a volume AcOEt. The organic phase is separated to obtain, after the usual work up, 0.09 g of methyl 3-(4-hydroxy-3,5-di-tert-butyl)phenyl-2-(2-tetrahydropyranyloxy)-2-carboxy-propanoate.

EXAMPLE 9

40 Ml of a LiOH solution in water-MeOH are added to a solution of 4.08 g of ethyl 3-(4-formyloxy-3,5-dimethoxy)phenyl-2-(2-tetrahydropyranyloxy)-2-ethoxy-carbonyl-propanoate in 20 ml of MeOH. The mixture is kept at r.t. for 12 hours, then evaporated to dryness. The residue is partitioned between water and AcOEt; the organic phase is washed with water to neutrality, then discarded. The alkali aqueous phases are combined, saturated with NaCl, added with the same volume of AcOEt and then acidified, under strong stirring, at pH 6–6.5, keeping the temperature of the reaction mixture at 5°–12° C. with outer cooling. The organic phase is quickly separated, washed with a small volume of a NaCl solution, dried to give, after evaporation of the solvent, 2.1 g of 3-(4-hydroxy-3,5-dinethoxy)phenyl-2-(2-tetrahydropyranyloxy)-2-carboxy-propanoic acid.

Analogously, the corresponding acetalic ethers: 2-(2-tetrahydropyranylether), 2-(1,4-dioxan-2-ylether) and 2-(1,4-oxathian-2-ylether) of the following acids are prepared:
3-(4-biphenyl)-2-hydroxy-2-carboxy-propanoic,
3-(3,4,5,-trimethoxy)phenyl-2-hydroxy-2-carboxy-propanoic,
3-(2-furyl)-2-hydroxy-2-carboxy-propanoic,
3-(2-thienyl)-2-hydroxy-2-carboxy-propanoic,
3-(α-naphthyl)-2-hydroxy-2-carboxy-propanoic,
3-(β-naphthyl)-2-hydroxy-2-carboxy-propanoic,
3-(3,5-dimethyl-isoxazol-5-yl)-2-hydroxy-2-carboxy-propanoic,
3-(4-hydroxy-3,5-di-tert-butyl)phenyl-2-hydroxy)-2-carboxy-propanoic,
2-hydroxy-2-methyl-1,3-propanedioic,
2-hydroxy-2-allyl-1,3-propanedioic,
2-hydroxy-2-(but-2-yn)-1,3-propanedioic,
2-hydroxy-2-cyclopentyl-1,3-propanedioic,
2-hydroxy-2-cyclopentylethyl-1,3-propanedioic,
2-hydroxy-2-cyclohexylmethyl-1,3-pr-panedioic,
2-hydroxy-2-cyclopentylethyl-1,3-propanedioic,
2-hydroxy-2-cyclohexylmethyl-1,3-propanedioic,
2-hydroxy-2-(nor-born-2-en-syn7-yl-methyl)-1,3-propanedloic.

EXAMPLE 10

Under nitrogen atmosphere and stirring, a solution of 2.64 g of methyl 2-(2-tetrahydropyranyloxy)-1,3-propanedioate in 25 ml of anhydrous THF, cooled to −78° C., is added dropwise to 20 ml of a 1M solution of sodium bis-trimethylsilylamide in THF. At the end of the addition, (about 20 min) the mixture is kept at −78° C. for 15 min. more, the temperature is left to reach −30° C. and stirring is continued for 30 min. more. After that, a solution of 3-tert-butoxycarbonylamino-propyl bromide (2.38 g) in 8 ml of anhydrous THF is added in 15 min, keeping stirring for 30 min at −30° C., then leaving to warm to r.t. and stirring is continued for 3 h. more. The mixture is concentrated to small volume (5–8 ml) under vacuum, diluted with an excess of a cold saturated solution of monobasic sodium phosphate and extracted repeatedly with AcOEt. The organic phases are combined, washed to neutrality with water, dried and evaporated to dryness. The residue is purified by chromatography on SiO$_2$ (eluent 20:80 cyclohexane-AcoEt) to give 3.06 g (76.6%) of methyl 5-tert-butoxycarbony-lamino-2-(2-tetrahydropyranyloxy)-2-methoxy-carbonyl-pentanoate.

A solution of 1.2 g of the compound in MeOE (8 ml), treated with 25 g of pTS acid for 6 hours at r.t., yields 0.82 g of methyl 5-tert-butoxycarbonylamino-2-hydroxy-2-methoxycarbonyl-pentanoate which, by treatment with MeOH and LiOH in MeOH—H$_2$O, is then converted into 5-tert-butoxycarbonyl-2-hydroxy-2-carboxy-pentanoic acid lithium salt (m.p.>250° C.).

A solution of 1.2 g of methyl 5-tert-butoxycarbonylamino-2-(2-tetrahydropyranyloxy)-2-methoxycarbonyl-pentanoate, by treatment with MeOH and LiOH in MeOH—H$_2$0, yields 5-tert-butoxycarbonylamino-2-(2-tetra-hydropyranyloxy)-2-carboxy-pentanoic acid lithium salt (m.p. 300° C.).

EXAMPLE 11

Using in the procedure of example 10 a halide selected from (R) and (S) (l-benzyl-piperidin-3-yl)methyl bromide, (1-BOC-piperidin-4-yl)methyl iodide, (R) and (S) (l-BOC-piperidin-3-yl)methyl bromide, 2-benzyloxycarbonylaminoethyl bromide, (R) and (S) (1-BOC-pyrrolidin-2-yl)methyl bromide, phenylthiomethyl chloride, 4-chloro-phenylthiomethyl chloride, 4-methoxy-phenylthiomethyl chloride and an acetalic ether selected from: 2-(2-tetrahydropyranylether), 2-(1,4–2-(1,4-dioxan-2-ylether) and 2-(1,4-oxathian-2-ylether) of the 2-hydroxy-1,3-propanedioic acid methyl, ethyl, allyl, p-methoxybenzyl esters, the esters of the corresponding acetalic ethers of the following acids are prepared:
(R) and (S) 3-(1-benzyl-piperidin-3-yl)-2-hydroxy-2-carboxy-propanoic,
(R) and (S) 3-(1-BOC-piperidin-3-yl)-2-hydroxy-2-carboxy-propanoic,
3-(1-BOC-piperidin-4-yl)-2-hydroxy-2-carboxy-propanoic,
3-(2-benzyloxycarbonylamino)-2-hydroxy-2-carboxy-propanoic,
(R) and (S) 3-(1-BOC-pyrrolidin-2-yl)-2-hydroxy-2-carboxy-propanoic,
3-(phenylthio)-2-hydroxy-2-carboxy-propanoic,
3-(4-chloro-phenylthio)-2-hydroxy-2-carboxy-propanoic,
3-(4-methoxy-phenylthio) -2-hydroxy-2-carboxy-propanoic.

EXAMPLE 12

4.3 g of ethyl 2-(2-tetrahydropyranyloxy)-1,3-propanedioate are added to 11 ml of a Na ethoxide solution (prepared from 0.72 g of Na) under stirring, shielding from humidity, keeping the temperature at 0° to 5° C. After 1 h, a solution of 2.4 g of 3-pyridyl-methyl chloride hydrochloride in 8 ml of EtOH is dropped therein. The reaction mixture, which turns suddenly red, is kept under stirring at r.t. for 24 hours more. EtOH is evaporated off and the residue is partitioned between AcOEt and a 20% solution of monobasic potassium phosphate in water. The organic phase is separated, evaporated to dryness and the residue (about 4 g) is dissolved with 16 ml of 2N HCl , keeping r.t. for 4 hours; ethyl tartronate is removed by extraction with AcOEt. From the aqueous phases, after alkalization to pH 8–8.5, subsequent extraction with AcOEt, the usual work up of the organic extract and subsequent chromatography on silica gel, 1.8 g of ethyl 3-(pyrid-3-yl)-2-hydroxy-2-ethoxycarbonyl-propanoate are obtained, oil, I.R.: 3500, 3000, 1740, 1590 cm$^{-1}$, TLC (SiO$_2$: one spot R$_f$: 0.24 eluent AcOEt), H-NMR(CDCl$_3$) δ (TMS): 1.2–1.3 t, 3.3 s, 4.15–4.3 q, 7.1-7.2 q, 7.6–7.65 m, 8.4–8.5 m.

A solution of 0.23 g of the compound in 4 ml of MeOH is treated at r.t. with 3.1 ml of a LIOH solution in MeOH—H$_2$O. After 12 hours, crystalline 3-(pyrid-3-yl) -2-hydroxy-2-carboxy-propanoic acid lithium salt precipitates, 0.13 g, m.p.>300° C., I.R.: 3400 (d) 1640 cm$^{-1}$.

EXAMPLE 13

A solution of 7.8 g of ethyl 2-(2-tetra-hydropyranyloxy)-1,3-propanedioate in 5 ml of EtOB is added to a solution of sodium ethoxide (12 ml, from 0.76 g of Na) under stirring and inert gas atmosphere; subsequently, a solution of 6 g of quinoline-2-methyl chloride in EtOH (40 ml) is added to the mixture which is stirred at r.t. for 8 h.; EtOH is evaporated off. The residue is partitioned between AcOEt and 5% aqueous monobasic potassium phosphate. The organic phases are combined, dried over sodium sulfate and evaporated to dryness. By crystallization from ethyl ether-hexane, 11.5 g of ethyl 3-(quinolin-2-yl)-2-(2-tetrahydropyranyloxy)- 2-ethoxycarbonyl-propanoate are obtained, m.p. 75–78° C; I.R.(nujol): 2900, 1740, 1600 cm$^{-1}$; H-NMR(CDCl$_3$) δ (TMS): 1.15–1.35 2t, 1.45–1.6 m, 1.6–1.7 m, 1.7–1.9 m, 3.35–3.5 m, 3.75–3.85 d, 3.85–3.95 m, 4.15–4.35 m, 5.2–5.3t, 7.4–7. 55 m, 7.6–7.75 m, 7.75–7.85 m, 7.9 –8.1 q.

A solution of 0.92 g of the compound in 10 ml of water and 2.4 ml of 2N HCl, kept at r.t. for 2 h., is repeatedly extracted with AcOEt (3×2 ml). The organic extracts are combined, washed with 0.2N EC1 (2×1 ml) and then discarded. The aqueous phases are combined and alkalinized to pH 8 with N KOH cooling to 3–8° C. The mixture is extracted with AcOEt (2×10 ml). The combined organic phases are washed with 2% monobasic potassium phosphate, dried over sodium sulfate. After evaporation of the solvent, the oily residue (0.85 g) is crystallized from ether ethyl-hexane to give 0.59 g of ethyl 3-(quinolin-2-yl) -2-hydroxy-2-ethoxycarbonyl-propanoate, m.p. 71–72° C., I.R.(nujol): 2800, 1740, 1600 cm 1; HNMR(CDCl$_3$) δ (TMS): 1.15–1.3 t, 3.7 s, 4.2–4.3 q, 7.0 s, 7.3–7.4 d, 7.45–7.55 m, 7.65–7.75 m, 7.9–8.0 d, 8.1–8.2 d.

By hydrolysis with LIOH in MeOH—H20 of 0.22 g of the latter ester at r.t. for 12 h, 0.16 g of 3-(quinolin-2-yl)-2-hydroxy-2-carboxy-propanoic acid lithium salt separate, m.p.>300° C.; I.R. (nujol): 3350, 1640, 1600 cm$^{-1}$; HNMR (D$_2$0) δ (TMS): 3.6 s, 7.4×7.6 m, 7.65–7.8 m, 7.8–8.0 m, 8.15–8.25 d.

A solution of ethyl 3-(quinolin-2-yl)-2-(2-tetrahydropyranyloxy)-2-ethoxycarbonyl-propanoate (0.5 g) in 5 ml of methanol is hydrolysed by treatment with a LiOH in MeOH—H$_2$0 solution. After 12 h at r.t., the solvent is evaporated off under vacuum and the residue is partitioned between AcOEt and an excess of a monobasic potassium phosphate saturated solution. The organic phase is separated, dried, evaporated to dryness to obtain 0.39 g of 3-(quinolin-2-yl)-2-(2-tetrahydropyranyloxy)-2-carboxy-propanoic acid.

EXAMPLE 14

7.1 G of methyl 2-(1,4-dioxan-2-yloxy)-1,3-propanedioate are added, under argon atmosphere, to 15 ml of a solution of sodium methoxide in MeOH (from 0.69 g of Na). The mixture is stirred for 20 min at r.t.; then, a solution of 5.61 g of 2-pyridylmethanesulfonate in 10 ml of MeOH is added thereto during 15 min. The mixture is kept at r.t. for 8 h, then evaporated to dryness. The residue is partitioned between AcOEt and a 15% monobasic sodium phosphate aqueous solution. From the organic phase, after the usual work up and purification on a silica gel column (eluent 70:30 cyclohexane:AcOEt), 7.8 g of methyl 3-(pyrid-2-yl)-2-(1,4-dioxan-2-yloxy)-2-methoxycarbonyl-propanoate.

1 g of the compound is hydrolysed in MeOH with LiOH in MeOH—H$_2$0 to give 0.79 g of 3-(pyrid-2-yl)-2-(1,4-dioxan-2-yloxy)-2-carboxy-propanoic acid lithium salt, m.p.>250° C.

2.8 g of methyl 3-(pyrid-2-yl)-2-(1,4-dioxan-2-yloxy)-2-methoxycarbonyl-propanoate are dissolved in 10 ml of water and 4 ml of 2N H$_2$so$_4$; the solution is kept at r.t. for 8 h and is then extracted with AcOEt (2×2 ml). The combined organic phases are extracted again with water (2 ml), then discarded. From the combined aqueous phases, after neutralization to pH 8.5 with N NaOH and extraction with AcOEt, 1.88 g of methyl 3-(pyrid-2-yl) -2-hydroxy-2-methoxy-carbonyl-propanoate are obtained, m.p. 118–123° C., H-NMR (CDCl$_3$) δ (TMS) 3.5 s, 3.8 s, 6.6–6.7 broad s, 7.1–7.3 m, 7.6–7.75 m, 8.4–8.5 d.

A solution of 0.69 g of said compound in 12 ml of MeOH is hydrolysed at r.t. with 9.3 ml of the LIOH in MeOH—H$_2$O solution, to give 0.4 g of 3-(pyrid-2-yl)-2-hydroxy-2-carboxypropanoic acid lithium salt, m.p.>300° C., I.R. (nujol) 3400, 1640 cm$^{-1}$, HNMR (D$_2$0) & (TMS): 3.4 s, 7.2–7.35 m, 7.65–7.8 m, 6.3–8.4 m.

EXAMPLE 15

240 Mg of tris(hydroxymethyl)aminomethane are added to a solution of 0.26 mg of 3-(quinolin-2-yl)-2-hydroxy-2-carboxy-propanoic acid in 4 ml of EtOH. The mixture is diluted with ethyl ether, and the 3-(quinolin-2-yl)-2-hydroxy-2-carboxy-propanoic acid bistromethamine salt separates.

EXAMPLE 16

A solution of 3.4 g of 2-methoxyethyl 2-(2-tetrahydropyranyloxy)-2-((2-methoxyethyl)carbonyl)-propanoate in 2-methoxyethanol (8 ml) is treated at r.t. with 25 mg of pTS acid for 8h. The mixture is evaporated to small volume, thoroughly diluted with water and extracted with AcOEt. From the organic phase, 2.5 g of 2-methoxyethyl 2-hydroxy-2-((2-methoxyethyl)carbonyl)-propanoate are recovered, dissolved in dichloromethane, reacted with 1.3 g of 1,4-oxathi-2-ene and 25 mg of pTS acid for 8 h at r.t., shielded from humidity. 0.3 ml of pyridine are added, the mixture is concentrated to small volume and chromatographed on silica gel (20:80:0.1 hexane-AcOEt-Pyr) to obtain 3.4 g of 2-methoxyethyl 2-(1,4-oxathian-2-ylether)-2-( (2-methoxyethyl)carbonyl)-propanoate.

EXAMPLE 17

20 Mg of pTS acid are added to a solution of 1.6 g of ethyl 5-tert-butoxycarbonylamino-2-hydroxy-2-ethoxycarbonyl-pentanoate in 12 ml of 1,4-diox-2-ene. After 5 h. at r.t., 0.3 ml of pyridine are added, the excess reagent is distilled under vacuum and the residue is chromatographed on silica gel, to give 1.75 g of ethyl 5-tert-butoxycarbonylamino-2-(1,4-dioxan-2-yl-oxy)-2-ethoxycarbonyl-pentanoate.

EXAMPLE 18

Using in the procedure of examples 2, 3, 10, 12 and 14 a suitable halide or sulfonic ester selected from the group of 4-pyridylmethyl, 7-chloro-2-quinolinemethyl, 4-(2-quinolinemethoxy)-benzyl, 3-(2-quinolinemethoxy)benzyl, 7-(2-quinolinemethoxy)-β-naphthylmethyl, 7-(7-chloro-2-quinolinemethoxy)-β-naphthylmethyl, 1,3-dioxolan-2- methyl, 7-methoxy-cumarin-4-methyl, 6,7-dimethoxy-cumarin-4-methyl, 2-(1,3-dioxolan-2-yl)ethyl, by reaction with an acetalic ether: 2-(2-tetrahydropyranylether), 2-(1,4-dioxan-2-ylether), 2-(1,4-oxathian-2-ylether) of a 2-hydroxy-1,3-propanedioic acid ester (methyl, ethyl, allyl, p-methoxybenzyl) the corresponding esters of the following acids are prepared:

3-(4-pyridyl)-2-(2-tetrahydropyranyloxy)-2-carboxy-propanoic,
3-(7-chloro-quinolin-2-yl)-2-(2-tetrahydropyranyloxy)-2-carboxy-propanoic,
3-(7-chloro-quinolin-2-yl)-2-(1,4-dioxan-2-yloxy)-2-carboxy-propanoic,
3-(4-(2-quinolinemethoxy) phenyl)-2-(2-tetrahydropyranyloxy)-2-carboxy-propanoic,
3-(4-(2-quinolinemethoxy)phenyl)-2-(1,4-dioxan-2-yloxy)-2-carboxy-propanoic,
3-(7-(2-quinolinemethoxy)B-naphthyl)-2-(2-tetrahydropyranyloxy)-2-carboxy-propanoic,
3-(4-(7-chloro-2-quinolinemethoxy)phenyl)-2-(2-tetrahydropyranyloxy)-2-carboxy-propanoic,
3-(7-(7-chloro-2-quinolinemethoxy)B-naphthyl)-2-(2-tetrahydropyranyloxy)-2-carboxy-propanoic,
3-(1,3-dioxolan-2-yl)-2-(2-tetrahydropyranyloxy)-2-carboxy-propanoic,
4-(1,3-dioxolan-2-yl)-2-(2-tetrahydropyranyloxy)-2-carboxy-butanoic,
4-(1,3-dioxolan-2-yl)-2-(1,4-dioxan-2-yloxy)-2-carboxy-butanoic,
3-(7-methoxy-cumarin-4-yl)-2-(2-tetrahycropyranyloxy)-2-carboxy-propanoic,
3-(6,7-dimethoxy-cumarin-4-yi)-2-(2-tetrahydropyranyloxy)-2-carboxy-propanoic, which can then be converted into the corresponding free and/or desacetalyzed acids to give the hydroxy esters and finally hydrolysed to give the corresponding hydroxy acids and the lithium and/or tromethamine salts thereof.

EXAMPLE 19

According to the process described by P. G. Baraldi et al., J. Heterocyclic Chem., 19, 557, 1982, a solution of an aldehyde selected from the group of benzaldehyde, 4-hydroxy-benzaldehyde, 3,4,5-trimethoxy-benzaldehyde, 3,5-dimethoxy-4-hydroxy-benzaldehyde, 3,5-dimethyl-4-hydroxy-benzaldehyde, 3,5-di-tert-butyl-4-hydroxy-benzaldehyde (0.0135 mmole) in 20 ml of dry dichloromethane, cooled at 0° C., is added with 1 g of anhydrous magnesium sulfate, 3.1 ml of triethylamine and 0.0135 mmole of an aminoalkylhalide hydrohalide selected from the group of 2-bromoethylamine hydrobromide, 3-bromopropylamine bromide hydrobromide, 4-aminobutyl chloride hydrochloride. The suspension is stirred overnight at r.t., concentrated under vacuum, added with Et$_2$O (100 ml) and then washed with 2×25 ml of a NaCl saturated solution. By evaporation of the solvent, the corresponding Schiff bases are obtained, as a yellow oil (I.R. 1660 cm$^{-1}$).

0.018 Mmoles of mercaptoacetic acid are added to a solution of the resulting imines in benzene (30 ml) and then is refluxed for 15 h, removing the formed water whith a Dean Stark apparatus. After evaporation to dryness, the residue is purified by chromatography on silica gel column, eluent cyclohexane-AcOEt, to obtain the corresponding (2-phenyl-4-oxo-thiazolidin-3-yl)-alkyl-halides:

2-(2-phenyl-4-oxo-thiazolidin-3-yl)-ethyl bromide,
3-(2-phenyl-4-oxo-thiazolidin-3-yl)-propyl bromide,
4-(2-phenyl-4-oxo-thiazolidin-3-yl)-butyl chloride,
2-(2-(4-hydroxy-phenyl )-4-oxo-thiazolidin-3-yl )-ethyl bromide,
2-(2-(3,5-dimethyl-4-hydroxy-phenyl)-4-oxo-thiazolidin-3-yl)-ethyl bromide,
2-(2-(3, 5-di-te rt-butyl-4-hydroxy-phenyl) -4-oxo-thiazolidin-3-yl)-ethyl bromide,
2-(2-(3,5-dimethoxy-4-hydroxy-phenyl)-4-oxo-thiazolidin-3-yl)-ethyl bromide,
2-(2-(3,4,5-trimethoxy-phenyl)-4-oxo-thiazolidin-3-yl)-ethyl bromide.

0.5 g of 2-(2-(4-hydroxy-phenyl)-4-oxo-thiazolidin-3-yl)-ethyl bromide dissolved in 2 ml of pyridine are treated at r.t. overnight with 0.6 ml of acetic anhydride. After thorough dilution with water, neutralization to pH 7.2 with diluted sulfuric acid, extraction with Et$_2$O, and evaporation of the solvent, 0.51 g of 2-(2-(4-acetoxy-phenyl)-4-oxo-thiazolidin-3-yl)-ethyl bromide are recovered. Analogously, the following compounds are prepared:

2-(2-(3,5-dimethyl-4-acetoxy-phenyl)-4-oxo-thiazolidin-3-yl)-ethyl bromide,
2-(2-(3,5-di-tert-butyl-4-acetoxy-phenyl)-4-oxo-thiazolidin-3-yl)-ethyl bromide,
2-(2-(3,5-dimethoxy-4-acetoxy-phenyl)-4-oxo-thiazolidin-3-yl)-ethyl bromide.

Using in the procedure of examples 2, 3 and 10 a suitable (2-phenyl-4-oxo-thiazolidin-3-yl)-alkyl halide, as prepared above, having any phenol groups present protected, by reaction with a suitable acetalic ether:

2-(2-tetrahydropyranylether), 2-(1,4-dioxan-2-ylether),
2-(11,4-oxathian-2-ylether) of 2-hydroxy-1,3-propanedioic acid methyl, ethyl, allyl and p-methoxybenzyl esters, the esters of the corresponding acetalic ethers of the following acids are prepared:

4-(2-phenyl-4-oxo-thiazolidin-3-yl)-2-hydroxy-2-carboxy-butanoic,
5-(2-phenyl-4-oxo-thiazolidin-3-yl)-2-hydroxy-2-carboxy-pentanoic,
6-(2-phenyl-4-oxo-thiazolidin-3-yl)-2-hydroxy-2-carboxy-hexanoic,
4-(2-(4-acetoxy-phenyl)-4-oxo-thiazolidin-3-yl)-2-hydroxy-2-carboxy-butanoic,
4-(2-(3,5-dimethyl-4-acetoxy-phenyl)-4-oxo-thiazolidin-3-yl)-2-hydroxy-2-carboxy-butanoic, 4-(2-(3,5-di-tert-butyl-4-acetoxy-phenyl 4-oxo-thiazolidin-3-yl)-2-hydroxy-2-carboxy-butanoic,
4-(2-(3, 5-dime thoxy-4-acetoxy-phenyl) -4-oxo-thiazolidin-3-yl)-2-hydroxy-2-carboxy-butanoic.
4-(2-(3, 4, 5-trimethoxy -phenyl)-4-oxo-thiazolidin-3-yl) 2-hydroxy-2-carboxy-butanoic.

When subjected to a selective transesterification according to the process of example 8, by transeterification in anhydrous MeOH/potassium carbonate, starting from a suitable acetalic ether of:

methyl 4-(2-(4-acetoxy-phenyl)-4-oxo-thiazolidin-3-yl)-2-hydroxy-2-methoxy-carbonyl-butanoate,
methyl 4-(2-(3,5-dimethyl-4-acetoxy-phenyl)-4-oxo-thiazolidin-3-yl)-2-hydroxy-2-methoxycarbonyl-butanoate,
methyl 4-(2-(3,5-di-tert-butyl-4-acetoxy-phenyl)-4-oxo-thiazolidin-3-yl)-2-hydroxy-2-methoxycarbonyl-butanoate,
methyl 4-(2-(3 5-dimethoxy-4-acetoxy-phenyl)-4-oxo-thiazolidin-3-yl)-2-hydroxy-2-methoxycarbonyl-butanoate, the corresponding acetalic ethers of the methyl esters of the following acids are prepared:
4-(2-(4-hydroxy-phenyl)-4-oxo-thiazolidin-3-yl)-2-hydroxy-2-carboxy-butanoic,
4-(2-(3 5-dimethy 1-4-hydroxy-phenyl)-4-oxo-thiazolidin-3-yl)-2-hydroxy-2-carboxy-butanoic, 4-(2-(3,5-di-tert-butyl-4-hydroxy-phenyl)-4-oxo-thiazolidin-3-yl)-2-hydroxy-2-carboxy-butanoic,
4-(2-(3,5-dimethoxy-4-hydroxy-phenyl)-4-oxo-thiazolidin-3-yl)-2-hydroxy-2-carboxy-butanoic,
which, if desired, are converted into the corresponding free and/or desacetalized acids, to give the corresponding esters and finally hydrolysed to give the corresponding hydroxy acids or the lithium and/or tromethamine salts thereof.

EXAMPLE 20

38.5 g of 3-chloropropylamine hydrochloride are added under stirring to 320 ml of aqueous 1N NaOH and to 220 ml of THF. 73 Ml of tert-butyrlcarbonate in 30 min and 0.5 g of triethylbenzylammonium bromide are added to the mixture which is stirred for 24 h, then THF is distilled. The aqueous solution is acidified by dilution with a 10% $KHSO_4$ aqueous solution and extracted repeatedly with ethyl acetate. The organic extracts are combined, washed with water, dried over $Na_2So_4$ and evaporated to dryness to give 44 g of 3 tert-butoxycarbonylamino-propyl chloride. I.R.(C=O 1700 $cm^{-1}$) (—NH-3350 $cm^{-1}$) (C—Cl 780 $cm^{-1}$) TLC (5:15 AcOEt-hexane) Rf=0.53

EXAMPLE 21

0.5 G of triethylbenzylammonium chloride and 100 ml of N NaOH and 25 ml of tert-butylcarbonate are added, under stirring during 30 min., to a suspension of 18 g of 4-methoxycarbonyl-piperidine hydrochloride in 80 ml of THF. Stirring is maintained for 24 h, tetrahydrofuran is evaporated under vacuum, to obtain, after the usual work up, 23.4 g of 1-tert-butoxy-carbonyl-4-methoxycarbonyl-piperidine. 23 g of this compound are added to a suspension of 28.5 g of LiBr and 13.2 g of $NABH_4$ in 80 ml of diglyme. The mixture is heated to 50° C. for one hour, poured into water and acidified with N HCl.

After extraction with ethyl acetate, the usual washings and drying of the organic phase and evaporation of the solvent under vacuum, 17 g of (1-tert-butoxycarbonyl-piperidin-4-yl)-methanol are obtained which, by reaction with p-toluenesulfonyl chloride (15.9 g) in pyridine, give 26.5 g of (1-tert-butoxycarbonyl-piperidin-4-yl)-methanol p-toluenesulfonate.

A solution of 3.7 g of the compound is treated in acetone with a NaBr molar excess (5 g) to give 2.6 g of (l-tert-butoxy-carbonyl-piperidin-4-yl)-methyl bromide. Analogously, by reaction with a NaI excess, (1-tert-butoxycarbonyl-piperidin-4-yl)-methyl iodide is obtained.

EXAMPLE 22

6.1 Ml of TEA, 1 g of 4A molecular sieves then, dropwise, a solution of 4.2 ml of ethyl chloroformate are added to a solution of L-BOC-pipecolic acid in anhydrous THF (60 ml), cooled at −10° C. The mixture is stirred from −10 to −5° C. for 1 h, filtered and concentrated to half volume under vacuum. The resulting solution is then added to a suspension of 7.5 g of $NaBH_4$ in anhydrous THF (50 ml) cooled at −10° C. After 2 hours the mixture is diluted carefully with 150 ml of a 10% $KHSO_4$ solution, keeping the temperature at about 0° C. and then is repeatedly extracted with ethyl acetate. The organic phases are combined, washed repeatedly with a $NaHCO_3$ saturated solution and water. By evaporation of the solvent, 6.2 g of L-(1-BOC-piperidin-2-yl)-methanol, are obtained, which is then transformed into L-(l-BOC-piperidin-3-yl)-methyl bromide, in agreement to the process of example 21.

EXAMPLE 23

By reaction of L-BOC-prolinol ([δ]D−54.9, EtOH 2%; m.p. 59–60° C.) with triphenylphosphine and $CBr_4$, L-(1-BOC-pyrrolidin-2-yl)methyl bromide is obtained.

EXAMPLE 24

A suspension of 15 g of K tert-butylate in 50 ml of N-methyl-pyrrolidone is added under stirring to 21 ml of diethyl malonate, then a solution of 22 g of 3-tert-butoxycarbonylamino-propyl bromide in 5 ml of N-methylpyrrolidone is added dropwise, at about 40–50° C. and in a time of 15–20 min. Heating at 50° C. is continued for 18 h. more, then the reaction mixture is cooled, diluted with water (150 ml) and extracted with ethyl acetate. From the combined organic phases, after the usual work-up, by evaporation of the solvent, 42 g of the crude product are obtained which, after chromatography on silica gel (eluent 9:1 hexane-ethyl acetate) yield 32 g of ethyl 5-tert-butoxycarbonylamino-2-ethoxycarbonyl-pentanoate (ethyl 5-BOC-amino-2-ethoxycarbonyl-pentanoate), as an oil.

I.R. (neat): 3400, 300, 1710 $cm^{-1}$ H-NMR ($CDCl_3$): 1.2–1–3 (t); 1.4–1.45 (s); 1.45–1.6 (m); 1.85–1.95 (m); 3.05–3.2 (q); 3.15–3.4 (t); 4.1–4.25 (q); 4.6 (s). Analogously, starting from the corresponding malonic esters, the following compounds are prepared:
methyl 4-BOC-amino-2-methoxycarbonyl-butanoate,
ethyl 8-BOC-amino-2-ethoxycarbonyl-octanoate,
methyl 2-methoxycarbonyl-4-(pyrrolidin-l-yl)-butanoate,
methyl 2-methoxycarbonyl-4-(piperidin-1-yl)-butanoate,
methoxyethyl 2-methoxyethylcarbonyl-4-(morpholin-1-yl)-butanoate,
methyl (R)-2-methoxycarbonyl-4-(1-BOC-pyrrolidin-2-yl)-butanoate,
ethyl (S)-2-ethoxycarbonyl-4-(1-BOC-piperidin-2-yl)-butanoate,
ethyl (S)-2-ethoxycarbonyl-4-(1-BOC-piperidin-4-yl)-butanoate,
ethyl (S)-2-ethoxycarbonyl-4-(1-benzyl-piperidin-3-yl)-butanoate,
ethyl 2-ethoxycarbonyl-4-(pyrid-3-yl)-butanoate,
ethyl 2-ethoxycarbonyl-4-(pyrid-4-yl)-butanoate,
ethyl 2-ethoxycarbonyl-4-(pyrid-2-yl)-butanoate,
methyl (S)-2-methoxycarbonyl-4-(1-BOC-pyrrolidin-2-yl)-butanoate.

EXAMPLE 25

A solution of ethyl 5-BOC-amino-2-ethoxycarbonyl-pentanoate (4 g) in 10 ml of benzene is added, under stirring, to a suspension of 0.39 g of Na hydride (80% dispersion in mineral oil) in 20 ml of benzene. The mixture is kept at room temperature for 15 min., then is heated to 45° C. for about 30 min,. until a clear solution is obtained, which is cooled to 6–8° C., then is added with a solution of 3.3 g of benzoyl peroxide in 20 ml of benzene during about 1.15 hours. Stirring is continued for 30 min. more, then 0.4 g of triphenylphosphine are added. After 15 minutes more, the mixture is diluted with cold water. The organic phase is washed repeatedly with 5% $NaHCO_3$, water, 5% $KHSO_4$ and water, dried and evaporated to dryness to give 5.2 g of crude product. By chromatography on silica gel in 1:1 hexane :hexane-ethyl acetate gradient, 3.8 g of ethyl 5-BOC-amino-2-benzoyloxy-2-ethoxycarbonyl-pentanoate (oil) are obtained. TLC (10:1 $CH_2Cl_2$-$Et_2O$) Rf=0.5 I.R. (—NH—3400 $cm^{-1}$) (C=O 1740 $cm^{-1}$ broad peak) (aromatic ring 1600 $cm^{-1}$) NMR ($CDCl_3$/TMS): (δ)=1.25–1.35 t; 1.45 s; 1.55–1.75 m; 2.3–2.45 m; 3.1–3.25 q; 4.2–4.35 q; 4.55 s; 7.4–7.65 m; 8.05–8.15 m and 0.7 g of ethyl 5-BOC-amino-2-hydroxy-2-ethoxycarbonyl-pentanoate (oil) TLC (10:1 $CH_2Cl_2$-$Et_2O$) Rf=0.21 I.R.: (—OH and —NH—3400 $cm^{-1}$ broad peak) (C—O 1720 $cm^{-1}$ broad peak) NMR ($CDCl_3$/TMS): (δ)=1.2–1.35 t; 1.43 s; 1.45–1.6 m; 2.0–2.1 m; 3.05–3.2 q; 3.2–4.05 braod peak; 4.2–4.35 q; 4.6 s.

EXAMPLE 26

Using in the process of example 25 an alkyl malonate prepared according to the process of example 24, the following compounds are prepared:
methyl 4-BOC-amino-2-hydroxy-2-methoxycarbonyl-butanoate,
ethyl 8-BOC-amino-2-hydroxy-2-ethoxycarbonyl-octanoate,
methyl 2-methoxycarbonyl-2-hydroxy-4-(pyrrolidin-1-yl)-butanoate,
methyl 2-hydroxy-2-methoxycarbonyl-4-(piperidin-1-yl)-butanoate,
methoxyethyl 2-hydroxy-2-methoxyethylcarbonyl-4-(morpholin-1-yl)-butanoate,
methyl (R)-2-hydroxy-2-methoxycarbonyl-4-(1-BOC-pyrrolidin-2-yl)-butanoate,
ethyl (S)-2-hydroxy-2-ethoxycarbonyl-4-(1-BOC-piperidin-2-yl)-butanoate,
ethyl (S)-2-hydroxy-2-ethoxycarbonyl-4-(l-BOC-piperidin-4-yl)-butanoate,
ethyl (S)-2-hydroxy-2-ethoxycarbonyl-4-(l-benzyl-piperidin-3-yl)-butanoate,
ethyl 2-hydroxy-2-ethoxycarbonyl-4-(pyrid-3-yl)-butanoate,
ethyl 2-hydroxy-2-ethoxycarbonyl-4-(pyrid-4-yl-butanoate,
ethyl 2-hydroxy-2-ethoxycarbonyl-4-(pyrid-2-yl)-butanoate,
methyl (S)-2-hydroxy-2-methoxycarbonyl-4-(1-BOC-pyrrolidin-2-yl)-butanoate,
methyl 4-BOC-amino-2-benzoyloxy-2-methoxycarbonyl-butanoate,
ethyl 8-BOC-amino-2-benzoyloxy-2-ethoxycarbonyl-octanoate,
methyl 2-benzoyloxy-2-methoxycarbonyl-4-(pyrrolidin-1-yl)-butanoate,
methyl 2-benzoyloxy-2-methoxycarbonyl-4-(piperidinyl)-butanoate,
methoxyethyl 2-benzoyloxy-2-methoxyethylcarbonyl-4-(morphol in-1-yl) -butanoate,
methyl (R)-2-benzoyloxy-2-methoxycarbonyl-4-(1-BOC-pyrrolidin-2-yl)-butanoate,
ethyl (S)-2-benzoyloxy-2-ethoxycarbonyl-4-(1-BOC-piperidin-2-yl)-butanoate,
ethyl (S)-2-benzoyloxy-2-ethoxycarbonyl-4-(1-BOC-piperidin-4-yl)-butanoate,
ethyl (S)-2-benzoyloxy-2-ethoxycarbonyl-4-(1-benzyl-piperidin-3-yl)-butanoate,
ethyl 2-benzoyloxy-2-ethoxycarbonyl-4-(pyrid-3-yl)-butanoate,
ethyl 2-benzoyloxy-2-ethoxycarbonyl-4-(pyrid-4-yl)-butanoate,
ethyl 2-benzoyloxy-2-ethoxycarbonyl-4-(pyrid-2-yl)-butanoate,
methyl (S) -2-benzoyloxy-2-methoxycarbonyl-4-(-BOC-pyrrolidin-2-yl)-butanoate.

EXAMPLE 27

A mixture of 4 g of ethyl 5-BOC-amino-2-benzoyloxy-2-ethoxycarbonyl-pentanoate and 2 g of $K_2CO_3$ in 40 ml of anhydrous methanol, cooled to 0°–5° C., is stirred for 1 h. After filtration of the potassium carbonate excess, the solution is acidified to pH 6 with 2N HCl and filtered from the salts which separate. Solvent is evaporated off under vacuum and the residue is partitioned between cold water and ethyl acetate. The organic phase is washed repeatedly with a 5% $K_2CO_3$ cold solution and with water to neutrality, dried over sodium sulfate and evaporated to dryness. The residue (3 g) is eluted, purified on 30 g of silica gel, eluent hexane-ethyl acetate from 95:5 to 80:20, to give methyl benzoate and 1.8 g of methyl 5-BOC-amino-2-hydroxy-2-methoxycarbonyl-pentanoate (oil). TLC (4:6 AcOEt-hexane) Rf=0.19 I.R.: (—OH and —NH—3400 cm$^{-1}$ broad peak) (C═O 1730 cm$^{-1}$ broad peak) NMR (CDCl$_3$/TMS): (δ) 1.45 s; 1.45–1.6 m; 2.0–2.1 m; 3.05–3.2 q; 3.8 s; 4.6 s. By acidification of the basic extracts with 20% $KHSO_4$ and subsequent extraction with ethyl acetate, 0.17 g of 5-BOC-amino-2-hydroxy-2-methoxycarbonyl-pentanoic acid are obtained (oil) TLC (3:1:1 nBuOH-AcOH-H$_2$O) Rf=0.54

EXAMPLE 28

Using in the process of example 27 a 2-benzoyloxy derivative prepared according to the process of example 26, the following compounds are prepared:
methyl 4-BOC-amino-2-hydroxy-2-methoxycarbonyl-butanoate,
methyl 8-BOC-amino-2-hydroxy-2-methoxycarbonyl-octanoate,
methyl 2-hydroxy-2-methoxycarbonyl-4-(pyrrolidin-1-yl)-butanoate,
methyl 2-hydroxy-2-methoxycarbonyl-4-(piperidin-1-yl)-butanoate,
methyl 2-hydroxy-2-methoxyethylcarbonyl-4-(morpholin-1-yl)-butanoate,
methyl (R)-2-hydroxy-2-methoxycarbonyl-4-(1-BOC-pyrrolidin-2-yl)-butanoate,
methyl (S)-2-hydroxy-2-methoxycarbonyl-4-(1-BOC-piperidin-2-yl)-butanoate,
methyl (S)-2-hydroxy-2-methoxycarbonyl-4-(1-BOC-piperidin-4-yl)-butanoate,
methyl (S)-2-hydroxy-2-methoxycarbonyl-4-(1-benzyl-piperidin-3-yl)-butanoate,
methyl 2-hydroxy-2-methoxycarbonyl-4-(pyrid-3-yl)-butanoate,
methyl 2-hydroxy-2-methoxycarbonyl-4-(pyrid-4-yl)-butanoate,
methyl 2-hydroxy-2-methoxycarbonyl-4-(pyrid-2-yl)-butanoate,
methyl (S)-2-hydroxy-2-methoxycarbony,l-4-(J-BOC-pyrrolidin-2-yl)-butanoate;
and the hemiesters thereof:
4-BOC-amino-2-hydroxy-2-methoxycarbonyl-butanoic,
8-BOC-amino-2-hydroxy-2-methoxycarbonyl-Octanoic,
(S)-2-hydroxy-2-methoxycarbonyl-4-(1-BOC-piperidin-2-yl)-butanoic,
(S)-2-hydroxy-2-methoxycarbonyl-4-(1-BOC-piperidin-4-yl)-butanoic,
(S)-2-hydroxy-2-methoxycarbonyl-4-(1-benzyl-piperidin-3-yl)-butanoic, 2-hydroxy-2-methoxycarbonyl-4-(pyrid-3-yl)-butanoic, 2-hydroxy-2-methoxycarbonyl-4-(pyrid-4-yl)-butanoic, 2-hydroxy-2-methoxycarbonyl-4-(pyrid-2-yl)-butanoic, (R) and (S)-2-hydroxy-2-methoxycarbonyl-4-(1-BOC-pyrrolidin-2-yl)-butanoic.

EXAMPLE 29

0.3 g of LiOH.H$_2$O are dissolved in 1.5 ml of water and the solution is diluted with MeOH to a total volume of 10 ml. This solution, pre-cooled to 0°–50° C., is added to a solution of 1 g of methyl 5-BOC-amino-2-hydroxy-2-methoxycarbonyl-pentanoate in 10 ml of MeOH, cooled at 0° C. The mixture is kept for 24 h at 0°–5° C., under mild stirring. A white crystalline precipitate separates, which is filtered, washed with MeOH and dried to obtain 0.86 g of 5-BOC-amino-2-hydroxy-2-carboxy-pentanoic acid lithium salt (m.p.>300° C.) TLC (3:1:1 nBuOH—AcOH—H$_2$O) Rf=0.35 I.R.: (C=O 1700 cm$^{-1}$) (COO—1595 cm$^{-1}$, 1620 cm$^{-1}$) (—OH, —NH—3500–3300 cm$^{-1}$).

A solution of 0.5 g of the lithium salt in 2 ml of water, pre-cooled to 5°–8° C., is treated under stirring with 5 ml of pre-cooled ethyl acetate and acidified to pH 5–5.5 with a 5% KHSO$_4$ solution. Stirring is continued for some minutes, the organic phase is separated, dried over Mg sulfate and evaporated to dryness to obtain 0.39 g of 5-BOC-amino-2-hydroxy-2-carboxy-5-pentanoic acid: TLC (3:1:1 nBuOH—AcOH—H$_2$O) Rf=0.35

EXAMPLE 30

By hydrolysis with lithium hydrate, according to the process of example 29, starting from the esters and hemiesters of example 28, the following compounds are prepared as free acids and lithium salts thereof:
4-BOCamino-2-hydroxy-2-carboxy-butanoic,
8-BOCamino-2-hydroxy-2-carboxy-octanoic,
(S)-2-hydroxy-2-carboxy-4-(1-BOC-piperidin-2-yl)-butanoic,
(S)-2-hydroxy-2-carboxy-4-(1-BOC-piperidin-4-yl)-butanoic,
(R) and (S)-2-hydroxy-2-carboxy-4-(1-BOC-pyrrolidin-2-yl)-butanoic.

EXAMPLE 31

A solution of 0.45 g of methyl 2-hydroxy-2-methoxycarbonyl-4-(piperidin-1-yl)-butanoate in 6 ml of MeOH is hydrolysed at about 0° C., with 5 ml of a LiOH aqueous-methanolic solution. By filtration of the precipitate, 0.32 g of 4-(piperidin-1-yl)-2-hydroxy-2-carboxy-butanoic acid lithium salt are obtained. By elution of an aqueous solution of the salt on a ion exchange column [e.g. 10 ml of Biorad AG 4-XA (anionic)] and elution with water, after freeze-drying the eluate, 4-(piperidin-1-yl)-2-hydroxy-2-carboxybutanoic acid is obtained as the free acid:
Analogously, the lithium salts and the free acids of the following acids are obtained
2-hydroxy-2-carboxy-4-(pyrrolidin-1-yl)-butanoic,
2-hydroxy-2-carboxy-4-(morpholin-1-yl)-butanoic,
(S)-2-hydroxy-2-carboxy-4-(1-benzyl-piperidin-3-yl)-butanoic,
2-hydroxy-2-carboxy-4-(pyrid-3-yl)-butanoic,
2-hydroxy-2-carboxy-4-(pyrid-4-yl)-butanoic,
2-hydroxy-2-carboxy-4-(pyrid-2-yl)-butanoic.

EXAMPLE 32

Trifluoroacetic acid (1 ml) is added, at –5° to 0° C., to a solution of 1 g of methyl 5-BOC-amino-2-hydroxy-methoxycarbonyl-pentanoate in CH$_2$Cl$_2$. The mixture is kept overnight at 0° C., evaporated under vacuum to dryness in a bath kept at 0° to 15° C., diluted with anhydrous ethyl ether and re-evaporated to dryness repeatedly, then the residue is suspended in an ethyl ether-hexane mixture, placed in refrigerator for 24 h a –5°–0° C. The methyl 5-ammonium-2-hydroxy-2-methoxy-carbonyl-pentanoate trifluoroacetate is obtained, m.p.: 82°–85° C., TLC (3:1:1 nBuOH—H$_2$O—AcOH) Rf=0.32 I.R. (C=O 1680 cm$^{-1}$, 1730 cm$^{-1}$) (—OH,NH$_3$+3500–3100 cm$^{-1}$) NMR (DMSO/TMS): (δ)=1.45–1.65 m; 1.85–2.0 m; 2.75–2.9 t; 3.35 s; 3.7 s; 7.3–7.8 broad band. A precooled solution of 0.3 g of the salt in 1 ml of water is treated with ethyl acetate (4ml) and an excess of a 20% dibasic sodium phosphate solution. The organic phase is separated, dried and evaporated to dryness to give 0.2 g of methyl 5-amino-2-hydroxy-2-methoxycarbonyl-pentanoate. Analogously, the following tartronic esters are obtained as trifluoroacetates or free bases:
methyl 4-amino-2-hyd-roxy-2-methoxycarbonyl-butanoate,
methyl 8-amino-2-hydroxy-2-methoxycarbonyl-octanoate,
methyl (R) -2-hydroxy-2-methoxycarbonyl-4-(pyrrolidin-2-yl)-butanoate,
methyl (S)-2-hydroxy-2-methoxycarbonyl-4-(piperidin-2-yl)-butanoate,
methyl (S)-2-hydroxy-2-methoxycarbonyl--4-(piperidin-4-yl)-butanoate,
methyl (R)-2-hydroxy-2-methoxycarbonyl-4-(piperidin-3-yl)-butanoate,
methyl (S)-2-hydroxy-2-methoxycarbonyl-4-(pyrrolidin-2-yl)-butanoate,
methyl (R)-2-hydroxy-2-methoxycarbonyl-4-(piperidin-2-yl)-butanoate,
methyl (R)-2-hydroxy-2-methoxycarbonyl--4-(piperidin-4-yl)-butanoate,
methyl (S)-2-hydroxy-2-methoxycarbonyl-4-(piperidin-$^3$-yl)-butanoate.

EXAMPLE 33

Using the procedure of example 31, by hydrolysis with LiOH in methanol and subsequent desalification by ion exchange on an anion resin, the following tartronic acids are obtained as the lithium salts and/or the free acids:
4-amino-2-hydroxy-2-carboxy-butanoic,
8-amino-2-hydroxy-2-carboxy--octanoic,
(R)-2-hydroxy-2-carboxy-4-(pyrrolidin-2-yl)-butanoic,
(S)-2-hydroxy-2-carboxy-4-(piperidin-2-yl)-butanoic,
(S)-2-hydroxy-2-carboxy-4-(piperidin-4-yl) -butanoic,
(R)-2-hydroxy-2-carboxy-4-(piperidin-3-yl)-butanoic,
(S)-2-hydroxy-2-carboxy-4-(pyrrolidin-2-yl)-butanoic,
(R)-2-hydroxy-2-carboxy-4-(piperidin-2-yl)-butanoic,
(R)-2-hydroxy-2-carboxy-4-(piperidin-2-yl)-butanoic,
(R)-2-hydroxy-2-carboxy-4-(piperidin-4-yl)-butanoic,
(S)-2-hydroxy-2-carboxy-4-(piperidin-3-yl)-butanoic,
5-amino-2-hydroxy-2-carboxy-pentanoic.

EXAMPLE 34

0.2 g of 4-BOC-amino-2-hydroxy-2-carboxy-butanoic acid are treated at –10°–5° C. with 0.2 ml of a 1:1 CH$_2$Cl$_2$:trifluoroacetic acid mixture, keeping this temperature for 12 hours. After careful evaporation of the solvents under vacuum, by crystallization from ethyl ether-hexane, 60 mg of 4-ammonium-2-hydroxy-2-carboxy-butanoic acid trifluoroacetate are obtained.

EXAMPLE 35

Analogously to the process of example 32, by reacting with trifluoroacetic acid the BOC-amino derivatives of examples 6 and 7, the following compounds are obtained:
ethyl 5-amino-2-benzoyloxy-2-ethoxycarbonyl-pentanoate,
methyl 4-amino-2-hydroxy-2-methoxycarbonyl-butanoate,
ethyl 8-amino-2-hydroxy-2-ethoxycarbonyl-octanoate,
methyl (R)-2-hydroxy-2-methoxycarbony1–4-(pyrrolidin-2-yl)-butanoate,
ethyl (S)-2-hydroxy-2-ethoxycarbonyl-4-(piperidin-2-yl) -butanoate,
ethyl (S)-2-hydroxy-2-ethoxycarbonyl-4-(piperidin-4-yl)-butanoate,
methyl (S)-2-hydroxy-2-methoxycarbonyl-4-(1-BOC-pyrrolidin-2-yl)-butanoate,
methyl 4-amino-2-benzoyloxy-2-methoxycarbonyl-butanoate, ethyl 8-amino-2-benzoyloxy-2-ethoxycarbonyl-octanoate,
methyl (R)-2-benzoyloxy-2-methoxycarbonyl-4-(pyrrolidin-2-yl)-butanoate,
ethyl (S)-2-benzoyloxy-2-ethoxycarbonyl-4-(piperidin-2-yl)-butanoate,
ethyl (S)-2-benzoyloxy-2-ethoxycarbonyl-4-(piperidin-4-yl)-butanoate,
methyl (S)-2-benzoyloxy-2-methoxycarbonyl-4-(pyrrolidin-2-yl)-butanoate.

EXAMPLE 36

An aqueous solution of 2-hydroxy-2-carboxy-5-amino-pentanoic acid lithium salt is neutralised at pH 7.05 with N HCl and added with a stoichiometric amount of a barium chloride solution. The mixture is kept at room temperature for 20 minutes, and precipitates the 2-hydroxy-2-carboxy-5-amino-pentanoic acid barium salt precipitates, which is filtered and dried under vacuum. The salt has m.p. 268°–270° C., with decomposition.

EXAMPLE 37

Analogously to example 25, the alkylation with 2-pyridyl-methanol p-toluenesulfonate of the diethyl malonate gives ethyl 2-ethoxycarbonyl-3-(pyrid-2-yl)propionate as an oil. I.R. (neat): 3000, 1720, 1600 cm$^{-1}$ H-NMR (CDCl$_3$/TMS): 1.15–1.25 (t); 3.3–3.4 (d); 4.05–4.15 (t); 4.1–4.25 (q); 7.05–7.25 (m); 7.5–7.65 (m); 8.45–8.55 (m).

The subsequent treatment with benzoyl peroxide (according to the procedure of example 25) gives: ethyl 2-benzoyloxy-2-ethoxycarbonyl-3-(pyrid-2-yl)propionate as an oil. I.R. (neat): 3000, 1720, 1600 cm$^{-1}$ H-NMR (CDCl$_3$/TMS): 1.2–1.35 (t); 3.9 (s); 4.25–4.4 (m); 7.05–7.15 (m); 7.35–7.45 (t); 7.45–7.6 (m); 7.9–8.0 (m); 8.45–8.5 (m).

The subsequent transesterification (MeOH/K$_2$CO$_3$), according to the procedure of example 27, allows to obtain: methyl 2-hydroxy-2-methoxycarbonyl-3-(pyrid-2-yl)-propanoate as a crystalline material, m.p. 121°–124° C.; I.R. (nujol): 2900, 1720, 1600 cm$^{-1}$ H-NMR (CDCl$_3$/TMS) : 3.5 (s); 3.75 (s); 6.7 (s); 7.1–7.25 (m); 7.6–7.7 (m); 8.4–8.5 (m).

We claim:

1. A compound of formula (I):

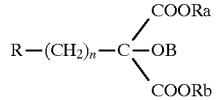

in which:
Ra and Rb are independently hydrogen, an alkali or alkaline-earth metal, an ammonium or C$_1$–C$_{10}$ alkylammonium cation, a C$_1$–C$_4$ alkyl group, a C$_1$–C$_4$ alkoxyethyl, allyl or p-methoxybenzyl group;
B is hydrogen or a C$_2$–C$_{12}$ acyl group;
R is a group of formula (II):

in which R$_1$ is hydrogen, C$_1$–C$_4$ alkyl, phenyl or benzyl; R$_2$ is tert-butoxycarbonyl (BOC), 9-fluorenylmethoxycarbonyl (FMOC), benzyloxycarbonyl, p-methoxybenzyloxycarbonyl, aminocarbonyl, or C$_1$–C$_4$ alkylaminocarbonyl;
R$_3$ is hydrogen, C$_1$–C$_4$ alkyl, tert-butoxycarbonyl (BOC), 9-fluorenylmethoxycarbonyl (FMOC), benzyloxycarbonyl, p-methoxybenzyloxycarbonyl, aminocarbonyl, or C$_1$–C$_4$ alkylaminocarbonyl;
m is zero or an integer from 1 to 3;
n is zero or an integer from 1 to 12;
or an optically active form, enantiomer, diastereomer thereof or a pharmaceutically acceptable salt thereof.

2. A compound according to claim 1, which is 5-tert-butoxycarbonylamino-2-hydroxy-2-carboxypentanoic acid.

3. A compound according to claim 1, which is 5-tert-butoxycarbonylamino-2-hydroxy-2-carboxypentanoic acid diethyl ester.

4. A compound according to claim 1, which is 5-tert-butoxycarbonylamino-2-hydroxy-2-carboxy-pentanoic acid dimethyl ester.

5. A compound according to claim 1, which is 5-tert-butoxycarbonylamino-2-hydroxy-2-carboxypentanoic acid monomethyl ester.

6. A compound according to claim 1, which is the lithium salt of 5-tert-butoxycarbonylamino-2-hydroxy-2-carboxypentanoic acid.

7. A compound according to claim 1, which is 5-tert-butoxycarbonylamino-2-benzoyloxy-2-carboxy-pentanoic acid diethyl ester.

8. A compound according to claim 1, which is 8-tert-butoxycarbonylamino-2-hydroxy-2-carboxyoctanoic acid diethyl ester.

9. A compound according to claim 1, which is 8-tert-butoxycarbonylamino-2-hydroxy-2-carboxyoctanoic acid dimethyl ester.

10. A compound according to claim 1, which is 8-tertbutoxycarbonylamino-2-hydroxy-2-carboxyoctanoic acid monomethyl ester.

11. A compound according to claim 1, which is 8-tert-butoxycarbonylamino-2-benzoyloxy-2-carboxyoctanoic acid diethyl ester.

12. A compound according to claim 1, which is 4-tert-butoxycarbonylamino-2-hydroxy-2-carboxybutanoic acid dimethyl ester.

13. A compound according to claim 1, which is 4-tert-butoxycarbonylamino-2-hydroxy-2-carboxybutanoic acid monomethyl ester.

14. A compound according to claim 1, which is 4-tert-butoxycarbonylamino-2-benzoyloxy-2-carboxybutanoic acid dimethyl ester.

15. A compound according to claim 1, selected from the group consisting of 4-tert-butoxycarbonylamino-2-hydroxy-2-carboxybutanoic acid, 8-tert-butoxycarbonylamino-2-hydroxy-2-carboxyoctanoic acid, and the lithium salts thereof.

16. A pharmaceutical composition containing as the active ingredient a compound of claim 1.

17. A method for treating osteoporosis, comprising administering to an animal in need of said treatment an osteoporosis-treatment effective amount of a compound of claim 1.

* * * * *